United States Patent [19]

Loots et al.

[11] Patent Number: 4,647,585

[45] Date of Patent: Mar. 3, 1987

[54] BICYCLOHEPTANE SUBSTITUTED ETHERS

[75] Inventors: Melanie J. Loots, Pennington; Steven E. Hall, Ewing Township, Mercer County; Peter W. Sprague, Pennington, all of N.J.

[73] Assignee: E. R. Squibb & Sons, Inc., Princeton, N.J.

[21] Appl. No.: 669,568

[22] Filed: Nov. 8, 1984

[51] Int. Cl.$^4$ .................. C07C 177/00; A61K 31/557
[52] U.S. Cl. ................. 514/530; 260/501.15; 514/573; 560/11; 560/15; 560/17; 560/60; 560/61; 560/120; 562/427; 562/466; 562/502
[58] Field of Search .................... 560/120, 11, 15, 17, 560/60, 61; 562/502, 427, 466; 514/573, 530; 260/501.15

[56] References Cited

U.S. PATENT DOCUMENTS 4,073,933 2/1978 Shimomura et al. .............. 424/299
4,143,054 3/1979 Sprague ........................ 260/346.82
4,436,934 3/1984 Larock ........................... 562/502

Primary Examiner—Robert Gerstl
Attorney, Agent, or Firm—Lawrence S. Levinson; Burton Rodney

[57] ABSTRACT

Bicycloheptane substituted ether prostaglandin analogs are provided having the structural formula

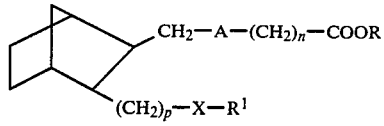

wherein X is O or

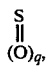

and including all stereoisomers thereof.

The compounds are cardiovascular agents useful, for example, in the treatment of thrombotic disease.

18 Claims, No Drawings

BICYCLOHEPTANE SUBSTITUTED ETHERS

DESCRIPTION OF THE INVENTION

The present invention relates to bicycloheptane substituted ether prostaglandin analogs which are cardiovascular agents useful, for example, in the treatment of thrombotic disease. These compounds have the structural formula

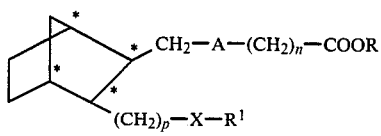

I and including all stereoisomers thereof, wherein A is —CH=CH— or —(CH$_2$)$_2$, n is 0 to 8, p is 0 to 5, X is O or

wherein q is 0, 1 or 2; R is H, lower alkyl, alkali metal or tris(hydroxymethyl)amino methane and R$^1$ is lower alkyl, aryl, aralkyl, cycloalkyl, cycloalkylalkyl, lower alkenyl or lower alkynyl.

Thus, the compounds of the invention include the following types of compounds:

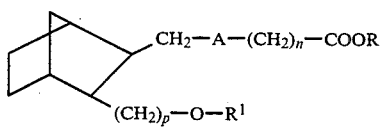

IA

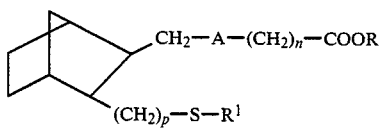

IB

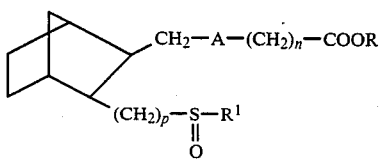

IC

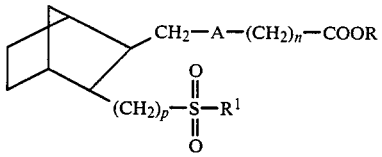

ID

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkyl-aryl substituent, a haloaryl substituent, a cycloalkyl substituent or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), and/or lower alkoxy groups.

The term "aralkyl", "aryl-alkyl" or "aryl-lower alkyl" as used herein by itself or as part of another group refers to lower alkyl groups as discussed above having an aryl substituent, such as benzyl.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The term "halogen" or "halo" as used herein by itself or as part of another group refers to chlorine, bromine, fluorine or iodine, with chlorine being preferred.

The terms "(CH$_2$)$_n$" and "(CH$_2$)$_p$" include a straight or branched chain radical having 1 to 8 carbons in the normal chain in the case of "(CH$_2$)$_n$" and 1 to 5 carbons in the normal chain in the case of "(CH$_2$)$_p$" and may contain one or more lower alkyl substituents. Examples of (CH$_2$)$_n$ and (CH$_2$)$_p$ groups include

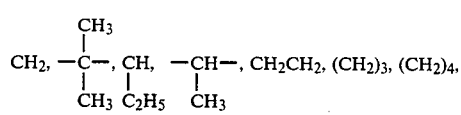

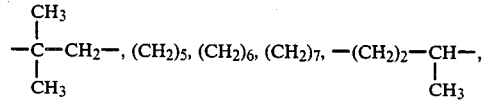

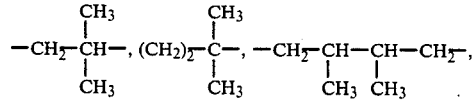

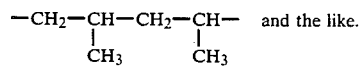

Preferred are those compounds of formula I wherein A is —CH=CH— or —CH₂—CH₂—, n is 3 to 5, p is 1, X is O or S, R is H, and R¹ is lower alkyl, such as hexyl, aryl, such as phenyl, or aralkyl such as benzyl.

The various compounds of the invention may be prepared as outlined below.

The 7-oxabicycloheptane ether compounds of formula I of the invention wherein X is O, p is 1, A is CH=CH or CH₂—CH₂, and n is 0 to 8, that is,

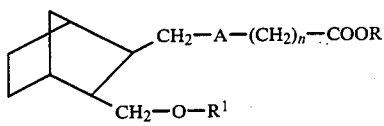
IE may be prepared starting with the alcohol II

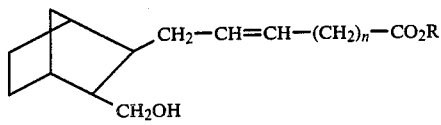
II (where R is lower alkyl)

which is subjected to an ether formation reaction wherein compound II is reacted with a strong base such as KOH, NaOH or LiOH and the like in the presence of an inert solvent, such as xylene, toluene, benzene or mesitylene and then after partial removal of solvent, reacting with a sulfonate compound of the structure A Mesyl-OR¹ or
A' Tosyl-OR¹ or a halide of the structure

A" R¹X (X is Cl or Br)

to form the ether

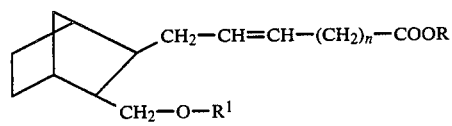
IF

Ether IF is then hydrolyzed by treating with strong base such as LiOH, KOH or NaOH to form the corresponding alkali metal salt and then neutralizing with a strong acid such as HCl or oxalic acid to form IG

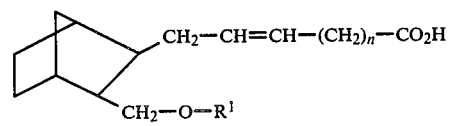
IG

Compounds of the invention wherein X is O, A is CH₂—CH₂ and n is 0 to 8 may be prepared by subjecting acid IG to hydrogenation by treating IG with hydrogen in the presence of a catalyst such as palladium and inert solvent such as tetrahydrofuran to form acid IH

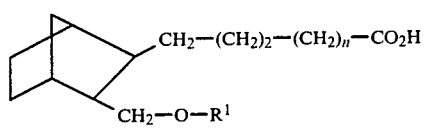
IH

Compounds of formula I wherein X is S, A is CH=CH, p is 1 may be prepared by starting with the hydroxymethyl compound II

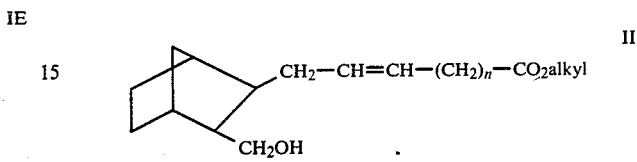
II and subjecting II to a tosylation reaction, for example, by reacting the hydroxymethyl compound with tosyl chloride in pyridine and methylene chloride to form the corresponding tosylate III

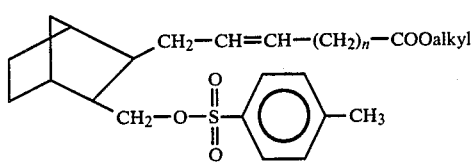
III

Thereafter, tosylate III is reacted with a thiol or mercaptan of the structure B

B  HSR¹ in the presence of potassium t-butoxide and a solvent such as tetrahydrofuran, dimethyl sulfoxide or dimethylformamide to form compounds of the invention of the structure IV

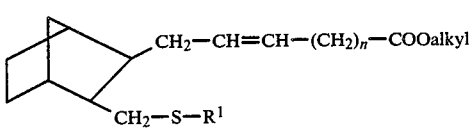
IV

Ester IV may then be hydrolyzed by treating with strong alkali metal base and then neutralizing with a strong acid, as described hereinbefore, to form the acid

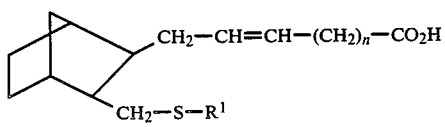
IJ

Compounds of the invention wherein p is 1, X is S, A is CH₂—CH₂ and n is 0 to 8 may be prepared by subjecting the hydroxymethyl compound II to hydrogenation by treating II with hydrogen in the presence of a catalyst such as palladium and an inert solvent such as tetrahydrofuran to form hydroxymethyl compound IIA

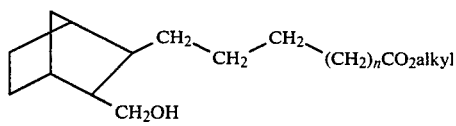
IIA

Compound IIA is then subjected to a tosylation reaction, for example, by reacting the hydroxymethyl compound with tosyl chloride in pyridine and methylene chloride to form the corresponding tosylate IIIA

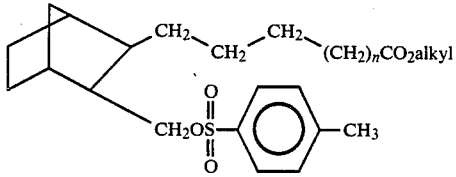
IIIA

Thereafter, tosylate IIIA is reacted with a thiol or mercaptan of the structure B, above, in the presence of potassium t-butoxide and a solvent, such as tetrahydrofuran, dimethylsulfoxide, or dimethylformamide to form compounds of the invention of structure IK

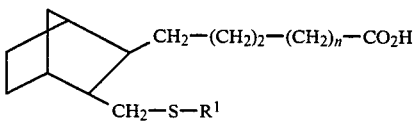
IK

Compounds of formula I wherein p is 2 to 5 may be prepared by subjecting hydroxymethyl compound II wherein A is CH=CH or hydroxymethyl compound IIA wherein A is —(CH$_2$)$_2$—

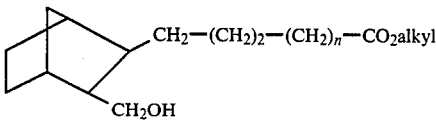
IIA (formed by reducing II by treating with hydrogen in the presence of a palladium on carbon catalyst) to a Collins oxidation by reacting II or IIA with chromium trioxide in the presence of a basic solvent such as pyridine or dichloromethane to form aldehyde V. Aldehyde V

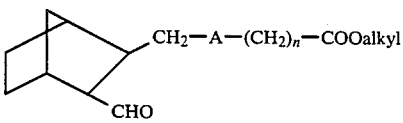
V wherein A is CH=CH or CH$_2$—CH$_2$, is subjected to a homologation sequence, such as a Wittig reaction with (C$_6$H$_5$)$_3$P$^+$Cl$^-$CH$_2$OCH$_3$ followed by hydrolysis, (p-1) times, to form aldehyde VI

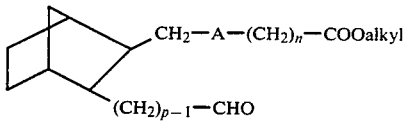
VI which is carried on to compounds of the invention where p is 2 to 5 by reducing aldehyde VI employing a reducing agent such as sodium borohydride in a solvent such as methanol to form alcohol ester VII

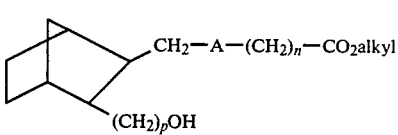
VII which is subjected to an etherification reaction with A, A' or A'' as described above or to a thioetherification reaction with thiol B after conversion of VII to its tosylate to form VIII

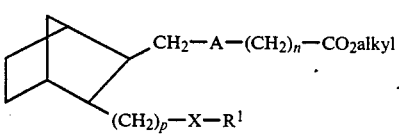
VIII

Compounds of formula IL wherein p is 0, that is

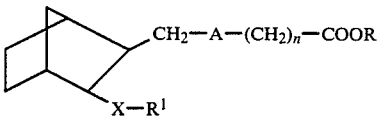
IL may be prepared as follows.
The lactone C

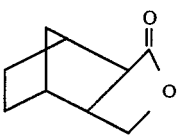
C is treated with methyl lithium in the presence of an inert organic solvent, such as tetrahydrofuran, under argon, at reduced temperatures of from about −50° to about −30° C. to form the corresponding hemiketal D

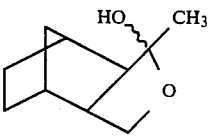
D

The hemiketal D is then subjected to silylation wherein hemiketal D in solution (such as with tetrahydrofuran) is treated with imidazole and t-butyldimethylsilyl chloride to form the corresponding cis ketone E

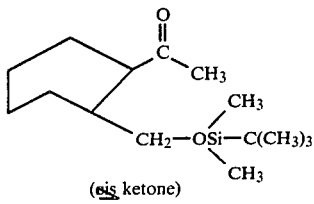
(cis ketone)

The cis ketone E may be used in the next step or may be epimerized to the corresponding trans ketone by reacting E with methyl alcohol and sodium methoxide under an inert atmosphere, such as argon, to form the trans silyloxy compound F which may be used in the next step

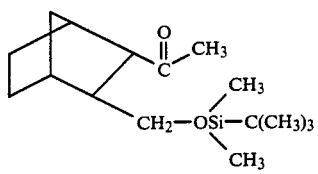

The cis ketone E or trans ketone F is oxidized by reaction with hydrogen peroxide and trifluoroacetic anhydride in methylene chloride in the presence of $Na_2HPO_4$ to form the corresponding trifluoroacetyl compound G

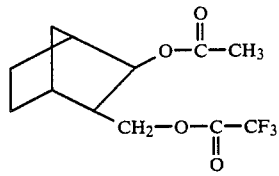

which is dissolved in tetrahydrofuran and treated with sodium bicarbonate solution to remove the trifluoroacetyl group and form the alcohol H

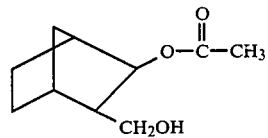

The alcohol H is then treated with 2-methoxyethoxymethyl chloride to form the hydroxy-protected compound J

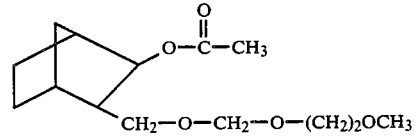

Where in the compounds of the invention of formula IL, X, which is directly attached to the ring, is to be oxygen, then compound H is converted to the appropriate lower side chain group $R^1$ by treating H with strong base such as sodium hydroxide or potassium hydroxide in the presence of an inert solvent such as xylene and a mesylate of the structure K MesylO-$R^1$ to form the protected compound L

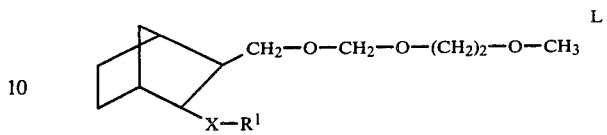

(where X is O).

The corresponding alcohol is next formed by treating L with titanium tetrachloride in the presence of methylene chloride at reduced temperatures to form the alcohol M

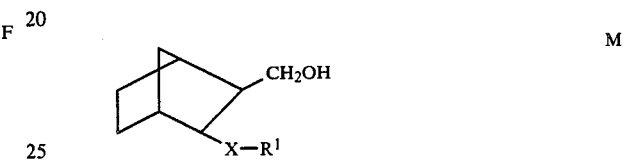

which is then oxidized to the aldehyde N by treating M with pyridinium chlorochromate in the presence of methylene chloride and sodium acetate

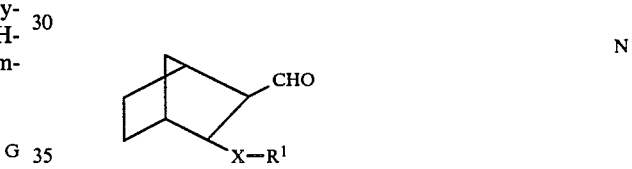

The aldehyde N is then subjected to a Wittig reaction by treating N with methoxymethylenetriphenyl phosphonium chloride in the presence of potassium t-amylate and an inert solvent such as tetrahydrofuran to form the vinyl ether compound O

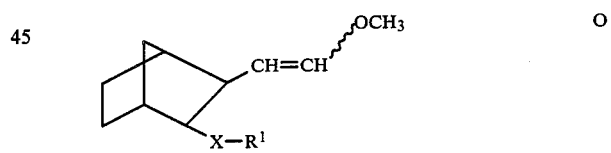

Vinyl ether O is then hydrolyzed by treating O with trifluoroacetic acid in the presence of an inert solvent such as tetrahydrofuran to form the aldehyde P

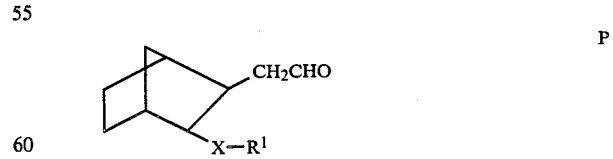

which is subjected to a Wittig reaction by treating aldehyde P with the reaction product of carboxyalkyltriphenyl phosphonium bromide $(Br(C_6H_5)_3P(CH_2)_nCOOH)$ and potassium t-amylate and subsequently with diazomethane to form the methyl ester IM

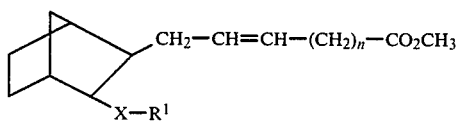
IM

The ester IM may then be hydrolyzed to the corresponding acid IN by treating IM with strong base such as lithium hydroxide, potassium hydroxide or sodium hydroxide

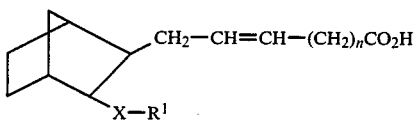
IN

Compounds of the invention wherein p is o and X is S may be prepared starting with a cooled solution of the hemiacetal CA

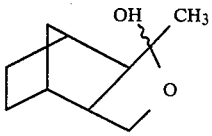
CA in methylene chloride. Anhydrous $Na_2HPO_4$ is added and then a peracid solution (formed by adding trifluoroacetic anhydride to a mixture of hydrogen peroxide and methylene chloride) is added and the reaction is maintained for 1 to 2 days to form a crude oxidation product. To a slurry of lithium aluminum hydride in ether under argon is added the crude oxidation product formed above to form diol R

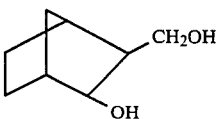
R

The diol R is tosylated by treating a solution of diol R, pyridine and methylene chloride cooled under argon with tosyl chloride in methylene chloride to form the tosylate S

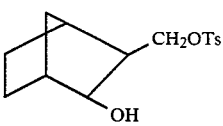
S which is heated with p-TsOH and dihydropyran to form the tetrahydropyran ether T

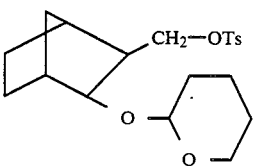
T

The tetrahydropyran ether T is treated with a solution of sodium cyanide in dimethylsulfoxide to form the nitrile U

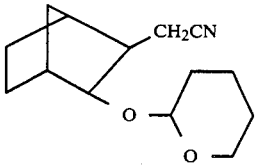
U which is treated with diisobutyl aluminum hydride (DIBAL) to form the acetaldehyde V

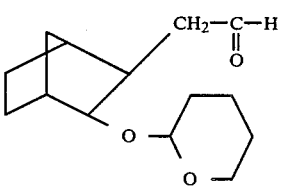
V

The acetaldehyde V is subjected to a Wittig rection employing carboxyalkyltriphenylphosphonium bromide $[Br(C_6H_5)_3P(CH_2)_nCOOH]$ in the presence of potassium t-amylate and an inert solvent such as toluene to form the vinyl ester W

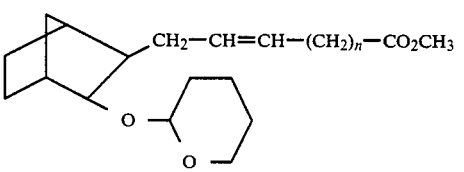
W which is then treated with Amberlyst 15 resin in the presence of methanol to form the alcohol ester Y

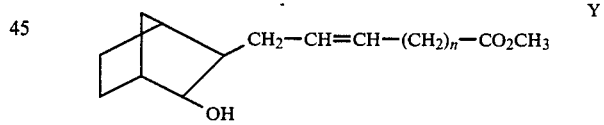
Y

The alcohol ester Y is treated with thiol acetic acid and a mixture of diisopropyl azo dicarboxylate (DIAD) and triphenyl phosphine in tetrahydrofuran to form the thioacetate Z

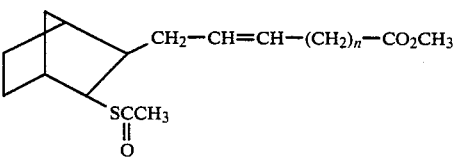
Z which together with a mercapto compound S
S HS—R¹
is treated with strong base, such as NaOH, KOH or LiOH in an inert solvent such as xylene to form the ester IM'

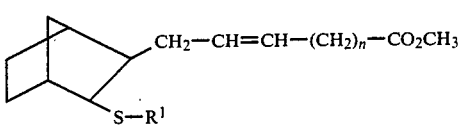
IM' which may be hydrolyzed to the corresponding acid IN'

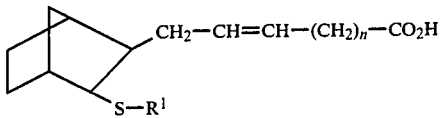
IN'

To form compounds wherein p is o, X is O or S and A is (CH₂)₂, compound IM, IN, IM' or IN' is hydrogenated by treatment with hydrogen in the presence of a catalyst such as palladium and inert solvent such as THF to form compound IO

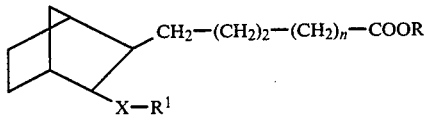
IO

The starting lactone C may be prepared by hydrogenating the anhydride UA

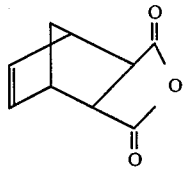
UA in the presence of a palladium catalyst and tetrahydrofuran to form the anhydride VA

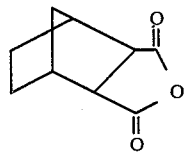
VA which may then be reduced by treating with sodium borohydride in the presence of tetrahydrofuran at reduced temperature to form lactone C.

To form compounds of formula I wherein X is

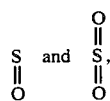

the sulfide derivative of formula I wherein X is S is subjected to an oxidation reaction, for example, by reacting same with sodium periodate, in the presence of methanol and tetrahydrofuran, to form the corresponding sulfinyl derivative

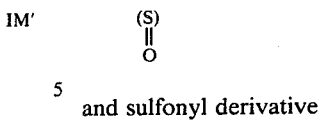

and sulfonyl derivative

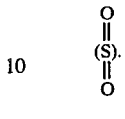

The sulfinyl and sulfonyl derivatives may be separated by chromatography or other conventional separation procedures.

The tris(hydroxymethyl)aminomethane salt of any of the acids of formula I of the present invention is formed by reacting a solution of such acid in an inert solvent such as methanol with tris(hydroxymethyl)aminomethane and thereafter the solvent is removed by evaporation to leave the desired salt.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

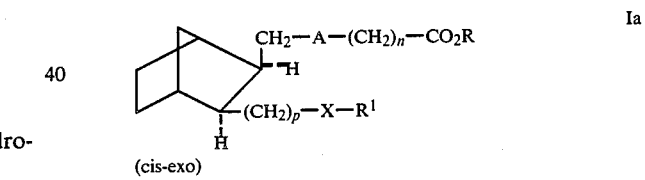
Ia
(cis-exo)

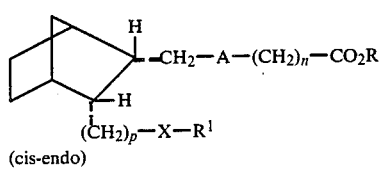
Ib
(cis-endo)

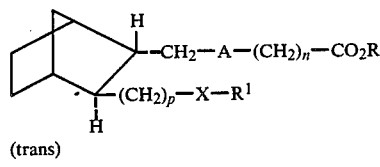
Ic
(trans)

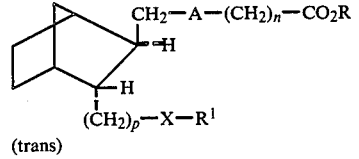
Id
(trans)

The nucleus in each of the compounds of the invention is depicted as

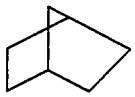

for matter of convenience; it will also be appreciated that the nucleus in the compounds of the invention may be depicted as

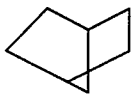

The compounds of this invention are cardiovascular agents useful as platelet aggregation inhibitors, such as inhibiting arachidonic acid-induced platelet aggregation (e.g., for treatment of thrombotic disease, such as inhibiting coronary or cerebral thromboses) and in inhibiting bronchoconstriction as induced by asthma. They are also selective thromboxane $A_2$ receptor antagonists, e.g., having a vasodilatory effect for treatment of myocardial ischemic disease, such as angina pectoris.

The compounds of the invention are also thromboxane synthetase inhibitors and thus may also be used for preventing gastrointestinal ulcer formation. They also increase the amount of endogenous prostacyclin $PGD_2$ and therefore may be used for controlling tumor cell metastasis or as antihypertensive agents.

The compounds of the invention are also arachidonic acid cyclooxygenase inhibitors. In addition, the compounds of the invention are useful as analgesic agents in the manner of aspirin and indomethacin as indicated by reaction thresholds to pressure in edematous hindpaws [Ref: Winter et al, J. Pharmacol, Exp. Ther. 150:165, 1965] and as antiinflammatory agents in mammals, as indicated by carrageenin-induced edema in the rat [Ref: Winter et al., J. Pharmacol., Exp. Ther. 141:369, 1963]. They may be used to decrease joint swelling, tenderness, pain and stiffness in conditions such as rheumatoid arthritis.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1α,2β(Z),3β,4α-7-[3-[(Hexyloxy)methyl]bicyclo-[2.2.1]hept-2-yl]-5-heptenoic acid A. exo-5-Norbornene-2,3-dicarboxylic anhydride 400 g (2.44 mole) of endo-5-norbornene-2,3-dicarboxylic anhydride was melted and heated in an open beaker to 190° for one hour and then cooled by pouring into a thin layer on the bottom of several crystallizing dishes. The resulting solid was scraped up before it cooled completely and recrystallized 5 times from benzene to give 75 g (0.046 mole) of pure exo-5-norbornene-2,3-dicarboxylic anhydride (19%), m.p. 143°.

B. (exo)-Hexahydro-4,7-Methanoisobenzofuran-1,3-dione

To a solution of 1.5 g (9.1 mmol) Part A cis exo isomer in 125 ml THF, was added 100 mg 10% Pd/C. The mixture was stirred under atmospheric hydrogen pressure until hydrogen uptake ceased, then filtered and concentrated to give a waxy white solid. This was dissolved in $Et_2O$ and reconcentrated to give 1.54 g of white solid (quantitative).

C. (3aβ,4α,7α,7aβ)-exo-Octahydro-4,7-methanoisobenzofuran-1(3H)one

To a suspension of 0.37 g (0.0098 mole) of $NaBH_4$ in 25 ml dry THF under $N_2$ was added all at once 1.54 g (0.0093 mole) of Part B compound. The reaction mixture was stirred at 0°–3° C. for 4 hours. The THF was removed in vacuo and the white solid obtained was added slowly to a beaker of ice with stirring. The cloudy white solution obtained was acidified to pH 2 and extracted with 6×15 ml $CH_2Cl_2$. The combined $CH_2Cl_2$ extracts were dried over $MgSO_4$, filtered and concentrated to give 1.13 g of title lactone as a clear oil (0.0083 mol, 89%).

D. (3aβ,4α,7α,7aβ)-exo-Octahydro-4,7-methanoisobenzofuran-1-ol

In a one-liter flask under $N_2$, 10.48 g (68.9 mmol) of the Part C lactone was dissolved in 150 ml B&J toluene and cooled to −70°. Over 1 hour, 144 ml of 1N diisobutyl aluminum hydride (DIBAL) in hexane was added (144 mmol) dropwise, keeping the reaction temperature at −65°. The mixture was stirred 30 minutes at −70°. A solution of 9 ml of acetic acid in 56 ml toluene was added over 10 minutes as the reaction temperature rose to −50°. It was allowed to warm to −30°, and 73 ml of 10% HCl was added, keeping the temperature below 0°. Then the reaction mixture was allowed to warm to room temperature.

The toluene/hexane and water layers were separated. The water layer was extracted 5×50 ml $CHCl_3$. Then the combined organic layers were washed with saturated $NaHCO_3$ and dried over $MgSO_4$. The solution was filtered and concentrated in vacuo to give 9 g of pale yellow oil (58.4 mmol) 85%.

E. (1α,3β,3β,4α)-3-(2-Methoxyethenyl)-bicyclo[2.2.1]heptane-2-methanol

At 0° under $N_2$, 41.96 g (0.122 mole) of methoxymethyl triphenyl phosphonium bromide (Aldrich) was suspended in 115 ml dry THF. Keeping the reaction temperature below 5°, 71.3 ml of 1.44M potassium t-amylate solution in toluene was added dropwise. The mixture was stirred 1 hour at 0°, giving a homogeneous, deep red solution.

A solution of 7.6 g (0.0493 mole) of Part D compound in 10 ml THF was added over 5 minutes. The reaction mixture was stirred 2 hours at room temperature. After cooling to 5°, 4.8 ml (3.78 g, 0.086 mole) of acetaldehyde was added. The temperature of the reaction rose to 13°. Water (100 ml) was added and the reaction mixture was neutralized to pH 7 with 10% HCl.

The organic and aqueous layers were separated. The aqueous layer was extracted 5 times with 75 ml $Et_2O$. The combined organics were dried over $MgSO_4$, filtered, and concentrated to a yellow oil. This was stirred with 150 ml diisopropyl ether. Precipitated triphenyl phosphine oxide was filtered off and the precipitate was washed well with ether. The filtrate was concentrated to a yellow oil (20 g). This was purified on a flash column, using 20% ethyl acetate in hexane as eluant to give 5.8 g of title enol ether (0.318 mol, 64.5%).

F. (4β,5α,8α,8aβ)-exo-Octahydro-5,8-methano-1H-benzopyran-3-ol

The Part E enol ether (0.81 g, 0.0044 mole) was stirred in 15 ml 20% aqueous trifluoroacetic acid for 1 hour under $N_2$. The mixture was diluted with 40 ml ether and neutralized by addition of solid $NaHCO_3$. The product was extracted with three 30 ml portions of ether. The combined ether extracts were dried over $MgSO_4$, filtered, and concentrated to give 0.68 g (0.004 mol) of title hemi-acetal (91%).

G. [1α,2β(Z),3β,4α]-7-[(3-Hydroxymethyl)bicyclo[2.2.1]hept-2-yl]-5-heptenoic acid, methyl ester At 0°, under $N_2$, 2.45 g (0.146 mole) of Part F hemi-acetal and 9.5 g (0.215 mole) of carboxybutyl triphenylphosphonium bromide were suspended in 60 ml toluene. Over 90 minutes, 29.3 ml of 1.42M potassium t-amylate, in toluene (0.417 mole) was added. The mixture was stirred for 30 minutes at 0°, then at room temperature overnight.

A solution of 2.33 ml (2.57 g, 0.043 mole) of acetic acid in 30 ml toluene was added dropwise while cooling the reaction mixture in an ice bath. Then 42 ml of water was added. A thick suspension formed. The mixture was acidified to pH 2.5 with concentrated HCl. It was then diluted with 42 ml ethyl acetate, 10 g of NaCl was added, and it was seeded with starting phsophonium salt and stirred for several hours. Precipitated phosphonium salt was then filtered off and washed well with ethyl acetate.

The toluene/ethyl acetate layer was separated from the water layer, and the water layer extracted with ethyl acetate. The combined organics were dried over $MgSO_4$, filtered, and concentrated to a thick oil. This was seeded with $(Ph)_3P=O$ and stirred several hours with 50 ml 5% $K_2CO_3$. It was filtered and reseeded several times to remove as much phosphorus impurity as possible. Then the aqueous filtrate was extracted 12 times with 50/50 toluene/ether. The aqueous layer was chilled and acidified slowly with concentrated HCl to pH 2.5. It was then extracted with ethyl acetate (2×50 ml, 2×25 ml). The combined ethyl acetate extracts were dried over $MgSO_4$, filtered, and concentrated to give 2.4 g of a yellow oil, which contained the desired product and phosphorus impurities.

This oil was dissolved in 20 ml ether/$CH_3OH$ and treated with diazomethane in ether until no evolution of $N_2$ was observed. Excess diazomethane was destroyed by addition of acetic acid. The ether solution was washed 2×5 ml saturated $NaCHO_3$, and dried over $MgSO_4$, filtered and concentrated in vacuo. The product was purified on a flash column, using 4:1 hexane:ethyl acetate (EA)/hexane as eluant, giving 1.2 g (0.0045 mol) of hydroxymethyl compound, 31% yield from the Part E enol ether.

H. [1α,2β(Z),3β,4α]-7-[3-[(Hexyloxy)methyl]bicyclo[2.2.1]hept-2-yl]-5-heptenoic acid, methyl ester
and I. [1α,2β(Z),3β,4α]-7-[3-[(Hexyloxy)methyl]bicyclo[2.2.1]hept-2-yl]-5-heptenoic acid, hexyl ester Under nitrogen, 13 ml of dry xylene and 0.51 g (9.1 mmole) of powdered KOH were combined, and 6 ml of xylene was distilled off. Another 4 ml of xylene was added and distilled off. Then a solution of 0.27 g title G hydroxymethyl compound (1 mmol) in 8 ml of dry xylene was added. A brown sticky precipitate appeared. A solution of 0.91 g (5 mmol) of hexyl mesylate in 5.5 ml of dry xylene was added, and 0.5 ml of xylene was distilled off. The reaction mixture was then refluxed 30 minutes. It thickened. TLC showed disappearance of starting material. The xylene mixture was added to 6 ml saturated $NH_4Cl$ solution in 2 ml of 1N HCl. The organic phase was separated. The aqueous phase was saturated with NaCl and extracted with ethyl acetate. The combined organics were dried over $MgSO_4$ and concentrated in vacuo to give 0.42 g yellow oil.

This oil was treated with excess $CH_2N_2$ [prepared from 4 g 1-methyl-3-nitro-1-nitrosoguanidine (MNNG), 50 ml $Et_2O$ and 12 ml 40% KOH)] to esterify any acid obtained by KOH saponification of the ester. Excess $CH_2N_2$ was destroyed by addition of acetic acid. The ethereal solution was washed with 3×15 ml saturated $NaHCO_3$ and dried on $MgSO_4$. It was concentrated and chromatographed on a flash column, using 5% ethyl acetate in hexane as eluent. This gave 150 mg of title H methyl ester and 100 mg of title I hexyl ester, total 0.6 mmole, 60% from title G.

J. [1α,2β(Z),3β,4α]-7-[3-[(Hexyloxy)methyl]bicyclo[2.2.1]hept-2-yl]-5-heptenoic acid Nitrogen was bubbled through a solution of 150 mg of title H methyl ester and 100 mg of title I hexyl ester (0.6 mmol total) in 1.8 ml THF and 0.38 ml $H_2O$, and then 0.76 ml of 1N LiOH was added. Methanol was added dropwise to make the reaction mixture homogeneous, and it was stirred overnight, when tlc showed that all ester had been saponified. The reaction mixture was poured into 10 ml saturated NaCl and acidified to pH 2.5. It was extracted 4×5 ml ethyl acetate and the combined extracts were dried over $MgSO_4$, filtered, concentrated and purified on a flash column to give 183 mg (0.54 mmol, 90%) of the title free acid.

While the C/H analysis on this compound was good, $^{13}C$ NMR showed the presence of an impurity which would not separate on tlc. This was presumed to be the 5,6-trans isomer.

EXAMPLE 2

(1α,2β,3β,4α)-7-[3-[(Hexyloxy)methyl]bicyclo[2.2.1]hept-2-yl]heptanoic acid

Example 1 compound (183 mg, 0.54 mmol) was dissolved in 5 ml EA with several drops of acetic acid and repeatedly hydrogenated until no double bond was visible in the 270 MHz $^1N$ NMR spectrum.

$^{13}C$ NMR showed that an impurity was still present. This is likely to be the trans-1 isomer, resulting from isomerization during the first Wittig reaction (in Example 1) in the preparation of the title G hydroxymethyl compound.

Chromatography on 50μ silica gel in the semi-prep column on the analytical hplc gave some separation of this impurity. It was possible to obtain purer samples of title compound by repeatedly chromatographing the material, using a solvent gradient from 0.25→0.5% $CH_3OH$ in $CH_2Cl_2$. The desired product was slightly more polar than the impurity. This chromatography eventually yielded 11 mg of pure title compound (6% yield from Example 1 compound).

EXAMPLE 3

[1α,2β(Z),3β,4α]]-7-[3-[(Hexylthio)methyl]bicyclo[2.2.1]hept-2-yl]-5-heptenoic acid A. [1α,2β(Z),3β,4α]-7-[3-(Hydroxymethyl)bicyclo[2.2.1]hept-2-yl]-5-heptenoic acid, methyl ester The above title A compound was prepared as described in Example 1, Part G.

B. [1α,2β(Z),3β,4α]-7-[3-[(Hexylthio)-methyl]-bicyclo[2.2.1]hept-2-yl]-5-heptenoic acid, methyl ester A solution of 270 mg (1.02 mmol) of Part A alcohol in 2 ml of dry pyridine was cooled to 0° C. To this stirred solution was added 295 mg (1.53 mmol) of tosyl chloride. After 4 hours, the temperature had risen to 5° C. The reaction mixture was diluted with 15 ml each of ether and saturated $NaHCO_3$ solution. The aqueous layer was extracted with 25 ml of ether. The combined ether layers were washed twice with 30 ml of 1N HCl, dried over $MgSO_4$, filtered, and concentrated in vacuo. The crude product was chromatographed on 32 g of silica gel using 4:1 hexane-ether as eluant. This gave 280 mg (66%) of pure tosylate along with 70 mg (16%) of a mixture of tosylate and its 5,6-double bond isomer.

TLC: silica gel, 3:2 Hexane-ether, $R_f=0.2$, iodine.

To a solution of 105 mg (0.93 mmol) of potassium t-butoxide in 10 ml of THF was added 0.45 ml (3.1 mmol) of 1-hexanethiol. To this stirred slurry was added a solution of 270 mg (0.64 mmol) of the above tosylate in 5 ml THF. The reaction mixture was heated to reflux for 5 hours. The cooled reaction mixture was partitioned between 30 ml each of saturated $NaHCO_3$ solution and ether. The aqueous layer was extracted with 2×30 ml of ether. The combined organic extracts were dried over $MgSO_4$, filtered and concentrated in vacuo. The crude product waas chromatographed on 30 g of silica gel using 4:1 hexane-ether as eluant to afford 230 mg (98%) of title B thioether.

C. [1α,2β(Z),3β,4α]-7-[3-[(Hexylthio)methyl]bicyclo[2.2.1]hept-2-yl]-5-heptenoic acid A solution of 220 mg (0.60 mmol) of Part B thioether in 15 ml of THF and 1.9 ml $H_2O$ was purged with a stream of Ar for 10 minutes. To this stirred solution was added 2.4 ml of 1N LiOH solution. This mixture was stirred vigorously for 7 hours at room temperature. The reaction mixture was partitioned between 25 ml each of brine and EtOAc. The aqueous layer was acidified to pH=2.5 by the addition of 1N HCl and then shook with the original EtOAc layer. The aqueous layer was extracted with 2×25 ml EtOAc. The combined EtOAc layers were dried over $MgSO_4$, filtered and concentrated in vacuo. Purification was effected by flash chromatography on 30 g of silica gel using 2:1 hexane-ether as eluant to afford title acid contaminated with a small amount of its 5,6-double-bond isomer. Rechromatography under the same conditions afforded 160 mg of pure title acid and 50 mg of a mixture of the double-bond isomers (95% total).

TLC: silica gel, 1:1 hexane-ether, $R_f=0.48$, iodine

EXAMPLE 4

[1α,2β(Z),3α,4α]-7-[3-(Heptyloxy)bicyclo[2.2.1]hept-2-yl]-5-heptenoic acid

A. (3aβ,4α,7α,7aβ)-exo-Octahydro-4,7-methanoisobenzofuran-1(3H)one (1) exo-5-Norbornene-2,3-dicarboxylic anhydride 400 g (2.44 mole) of endo-5-norbornene-2,3-dicarboxylic anhydride was melted and heated in an open beaker to 190° for one hour and then cooled by pouring into a thin layer on the bottom of several crystallizing dishes. The resulting solid was scraped up before it cooled completely and recrystallized 5 times from benzene to give 75 g (0.046 mole) of pure exo-5-norbornene-2,3-dicarboxylic anhydride (19%), m.p. 143°.

(2) exo-Hexahydro-4,7-methanoisobenzofuran-1,3-dione

To a solution of 1.5 g (9.1 mmol) Part A cis exo isomer in 125 ml THF, was added 100 mg 10% Pd/C. The mixture was stirred under atmospheric hydrogen pressure until hydrogen uptake ceased, then filtered and concentrated to give an oily white solid. This was dissolved in $Et_2O$ and reconcentrated to give 1.54 g of white solid (quantitative).

(3) (3aβ,4α,7α,7aβ)-exo-Octahydro-4,7-methanoisobenzofuran-1(3H)-one

To a suspension of 0.37 g (0.0098 mole) of $NaBH_4$ in 25 ml dry THF under $N_2$ was added 1.54 g (0.0093 mole) of Part A(2) compound, all at once, with some foaming. The reaction mixture was stirred at 0°-3° C. for 4 hours. The THF was removed in vacuo and the white solid obtained was added slowly to a beaker of ice, with stirring and fizzing. The cloudy white solution obtained was acidified to pH 2 and extracted 6×15 ml $CH_2Cl_2$. The combined $CH_2Cl_2$ extracts were dried over $MgSO_4$, filtered and concentrated to give 1.13 g of title lactone as a clear oil (0.0083 mole, 89%).

B. (3aβ,4α,7α,7aβ)-exo-Octahydro-4,7-methano-1-methyl-isobenzofuran-1-ol

To a stirred solution of 4.9 g (32.5 mmol) of Part A lactone in 360 ml of dry THF under argon at −78° C. is added dropwise 22 ml of 1.5M methyllithium solution over a period of 15 minutes. The reaction mixture is stirred at −78° C. for 35 minutes and then quenched with acetone. The reaction mixture is concentrated in vacuo to approximately 100 ml and diluted with EtOAc and saturated $NH_4Cl$ solution. The aqueous layer is saturated with NaCl and extracted with EtOAc (2×300 ml). The combined EtOAc extracts are dried ($MgSO_4$), filtered and concentrated in vacuo to give title hemiketal.

C. (1α,2β,3β,4α)-1-[3-[[[(1,1-Dimethylethyl)dimethylsilyl]oxy]methyl]bicyclo[2.2.1]hept-2-yl]-1-ethanone To a stirred solution of 14.8 g (88.2 mmol) of Part B hemiketal in 267 ml of dry DMF under argon is added 35.5 g (521 mmol) of imidazole. To this mixture is then added 31.4 g (208 mmol) of t-butyldimethylsilyl chloride. The reaction mixture is stirred at room temperature for 21 hours. The reaction mixture is partitioned between ether and $H_2O$. The aqueous layer is extracted with ether (2×1.4 l). The combined ether extracts are dried ($Na_2SO_4$), filtered and concentrated in vacuo. The resultant oil is chromatographed on silica gel 60 using a hexane-ether mixture as eluant to give title cis-ketone.

D. (1α,2α,3β,4α)-1-[3-[[[(1,1-Dimethylethyl)dimethylsilyl]oxy]methyl]bicyclo[2.2.1]hept-2-yl]-1-ethanone To a stirred solution of 24.8 g (87.8 mmol) of Part C cis-ketone in CH$_3$OH is added 326 mg (8.15 mmol) of sodium methoxide under argon. The reaction mixture is stirred at room temperature for 22 hours. The reaction mixture is concentrated in vacuo to approximately 100 ml and diluted with 700 ml of EtOAc. The resulting solution is washed with saturated NaHCO$_3$ solution (2×100 ml) and brine (1×150 ml). The organic layer is dried (MgSO$_4$), filtered and concentrated in vacuo to give title trans-ketone.

E. (1α,2α,3β,4α)-[3-[[[(1,1-Dimethylethyl)dimethylsilyl]oxy]methyl]bicyclo[2.2.1]heptan-2-ol, acetate (ester)

F. (1α,2β,3α,4α)-3-(Acetyloxy)bicyclo[2.2.1]heptane-2-methanol, trifluoroacetate and G. (1α,2β,3α,4α)-3-Hydroxybicyclo[2.2.1]heptane-2-methanol To a stirred slurry of 3.34 ml (138 mmol) of 90% H$_2$O$_2$ in 79 ml of dry CH$_2$Cl$_2$ at 0° C. is added dropwise 20.9 ml (149 mmol) of distilled trifluoroacetic anhydride over 20 minutes. This solution is stirred at 0° C. for 55 minutes. To a stirred slurry of 9.9 g (35.5 mmol) of Part D trans-ketone and 37.1 g of dry Na$_2$HPO$_4$ in 99 ml of dry CH$_2$Cl$_2$ at 0° C. is added the above peracid solution dropwise over 80 minutes. The resulting mixture is stirred at 0° C. for 5 hours and 30 minutes and then the solid (Na$_2$HPO$_4$) is removed by filtration. The filter cake is washed with CH$_2$Cl$_2$ (5×120 ml) and filtered. The filtrate is washed with 10% Na$_2$CO$_3$ solution (2×100 ml) and brine (1×200 ml). The organic layer is dried (MgSO$_4$), filtered and concentrated in vacuo. This is chromatographed on silica gel 60 using hexane-ether mixture as eluant to give title E compound, title F acetate and a mixture which contains corresponding title G diol.

H. (1α,2β,3α,4α)-3-(Acetyloxy)bicyclo[2.2.1]heptane-2-methanol

To a stirred solution of 8.75 g (31.3 mmol) of Part F acetate in 100 ml of freshly distilled THF is added 20 ml of H$_2$O and 10 ml of saturated NaHCO$_3$ solution. The reaction mixture is stirred at room temperature for 6 hours and 20 minutes at which time an additional 10 ml of saturated NaHCO$_3$ solution is added. The mixture is stirred for 45 minutes and another 10 ml of saturated NaHCO$_3$ solution is added. The mixture is stirred for an additional 25 minutes and poured into 200 ml of brine. The aqueous layer is saturated with NaCl and extracted with ether (4×250 ml). The combined ether extracts are dried (MgSO$_4$), filtered and concentrated in vacuo to give 5.41 g of crude alcohol. Purification is effected by flash chromatography on silica gel 60 using a CH$_3$OH/CH$_2$Cl$_2$ mixture as eluant to give title alcohol as an oil.

I. (1α,2α,3β,4α)-3-[[(2-Methoxyethoxy)methoxy]methyl]bicyclo[2.2.1]heptan-2-ol, acetate ester To a stirred solution of 2.99 g (16.2 mmol) of Part H alcohol in 25 ml of dry CH$_2$Cl$_2$ under argon is added 5.66 ml (32.5 mmol) of diisopropyl ethyl amine, followed by dropwise addition of 2.78 ml (24.4 mmol) of 2-methoxyethoxymethyl chloride. The reaction mixture is stirred at room temperature for 21 hours and then diluted with 300 ml of CHCl$_3$. The organic layer is washed with 1N HCl solution (2×50 ml), and saturated NaHCO$_3$ solution (1×100 ml). The organic layer is dried (MgSO$_4$), filtered and concentrated in vacuo. Purification is effected by flash chromatography on silica gel 60 using CH$_3$OH in CH$_2$Cl$_2$ as eluant to give title compound as an oil.

J. (1α,2α,3β,4α)-2-(Heptyloxy)-3-[[(2-methoxyethoxy)methoxy]methyl]bicyclo[2.2.1]heptane A mixture of 6.27 g (113 mmol) of powdered KOH in 170 ml of dry xylene is heated to reflux under argon atmosphere and 85 ml of xylene is removed by distillation. To this mixture is added a solution of 3.47 g (12.7 mmol) of Part I compound in 115 ml of dry xylene. The volume of the reaction mixture is reduced 100 ml by distillative removal of xylene. To the reaction mixture is then added a solution of 12.3 g (67.3 mmol) of n-heptyl mesylate in 90 ml of dry xylene. The reaction mixture is refluxed for 3 hours. The cooled reaction mixture is diluted with 200 ml of brine and extracted with EtOAc (5×200 ml). The combined EtOAc extracts are dried (Na$_2$SO$_4$), filtered and concentrated in vacuo. This is chromatographed on 120 g of silica gel 60 using 1:1 hexane-ether as eluant to give 7.08 g of crude ether. Final purification is effected by flash chromatography on silica gel 60 using hexane-ether eluant to give title ether.

K. (1α,2β,3α,4α)-3-(Heptyloxy)bicyclo[2.2.1]heptane-2-methanol

To a stirred solution of 1.88 g (5.76 mmol) of Part J MEM ether in 25 ml of dry CH$_2$Cl$_2$ under argon at 0° C. is added dropwise 3.28 g (17.3 mmol) of TiCl$_4$. The reaction mixture is stirred for 30 minutes and quenched with 12 ml of concentrated NH$_4$OH solution. The reaction mixture is diluted with 120 ml of H$_2$O and extracted with EtOAc (5×100 ml). The combined EtOAc extracts are dried (MgSO$_4$), filtered and concentrated in vacuo. Purification is effected by flash chromatography on 80 g of silica gel 60 using 1% CH$_3$OH in CH$_2$Cl$_2$ as eluant to give title heptyl ether alcohol as an oil.

L. (1α,2β,3α,4α)-3-(Heptyloxy)bicyclo[2.2.1]heptane-2-carboxaldehyde

To a stirred mixture of 2.94 g (17.6 mmol) of pyridinium chlorochromate and 0.22 g (2.73 mmol) of NaOAc in 55 ml of dry CH$_2$Cl$_2$ under argon at room temperature is added rapidly a solution of 1.31 g (5.45 mmol) of Part K heptyl ether alcohol in 16.5 ml of dry CH$_2$Cl$_2$. The reaction mixture is stirred for 1 hour and 30 minutes and diluted with 72 ml of ether. The organic solution is decanted and the insoluble black residue is washed with ether (2×100 ml) until the precipitate becomes granular. The combined organic solution is passed through a 3″ pad of Florisil which is then washed with ether (3×100 ml). The combined filtrates are concentrated in vacuo to give title aldehyde.

M. (1α,2α,3β,4α)-2-(Heptyloxy)-3-(2-methoxyethenyl)bicyclo[2.2.1]heptane

To a stirred solution of 3.28 g (9.56 mmol) of methoxymethylenetriphenylphosphonium chloride in 45 ml of dry THF under argon in an acetone-ice bath is added 4.97 ml (7.11 mmol) of 1.43M potassium t-amylate solution dropwise over 10 minutes. To this mixture is added a solution of 1.12 g (4.71 mmol) of Part L aldehyde in 23 ml of dry THF dropwise at 0° C. over 70 minutes. The reaction mixture is stirred at room temperature for 2 hours, cooled in an acetone-ice bath, and then quenched with 20 ml of acetaldehyde. The reaction mixture is diluted with 150 ml of saturated NH$_4$Cl solution and 50 ml of 1N aqueous HCl solution and extracted with ether (3×270 ml). The combined ether extracts are dried (MgSO$_4$), filtered and concentrated in vacuo. Purifica- N. (1α,2β,3α,4α)-3-(Heptyloxy)bicyclo[2.2.1]heptane-2-acetaldehyde To a stirred solution of 732 mg (2.76 mmol) of Part M vinyl ether in 7.4 ml of freshly distilled THF under argon is added 29.6 ml of 20% aqueous trifluoroacetic acid solution. The reaction mixture is stirred at room temperature for 3 hours and 10 minutes and then neutralized with solid NaHCO$_3$. The mixture is poured into 100 ml of H$_2$O and extracted with CH$_2$Cl$_2$ (4×80 ml). The combined CH$_2$Cl$_2$ extracts are dried (MgSO$_4$), filtered and concentrated in vacuo to give a colorless oil. This compound is dissolved in 30 ml of benzene and concentrated in vacuo to give title aldehyde as an oil.

O. [1α,2β(Z),3α,4α]-7-[3-(Heptyloxy)bicyclo[2.2.1]hept-2-yl]-5-heptenoic acid, methyl ester To a stirred solution of 1.96 g (4.43 mmol) of carboxybutyltriphenylphosphonium bromide in 35 ml of dry THF under argon at 0° C. is added dropwise 6.23 ml (7.91 mmol) of 1.27M of potassium t-amylate toluene solution. The mixture is stirred at 0° C. for an hour. To this homogeneous burgundy-red solution is added dropwise a solution of 663 mg (2.64 mmol) of Part N trans-aldehyde in 56 ml of dry THF over 80 minutes. The reaction mixture is allowed to warm to room temperature and is stirred for 22 hours and 10 minutes. The reaction mixture is cooled in an ice-bath and quenched with dropwise addition of 10 ml of glacial acetic acid. The mixture is poured into 100 ml of brine and extracted with EtOAc (4×100 ml). The combined EtOAc extracts are dried (MgSO$_4$), filtered and concentrated in vacuo. The residue is treated with 300 ml of diazomethane solution and excess diazomethane is destroyed by addition of HOAc. The mixture is concentrated in vacuo and chromatographed on silica gel 60 using a hexane-ether mixture as eluant to give the title methyl ester.

P. [1α,2β(Z),3α,4α]-7-[3-(Heptyloxy)bicyclo[2.2.1]hept-2-yl]-5-heptenoic acid

To a stirred solution of 346 mg (1.00 mmol) of Part O methyl ester in 54 ml of freshly distilled THF and 9.0 ml of H$_2$O is added 10.0 ml of 1N aqueous lithium hydroxide solution. The reaction mixture is purged with argon vigorously for 30 minutes and stirred at room temperature for 8 hours and 20 minutes. The reaction mixture is acidified to pH 3 by the addition of 1N aqueous HCl solution and poured into 80 ml of brine. The aqueous layer is saturated with NaCl and extracted with EtOAc (4×100 ml). The combined EtOAc extracts are dried (MgSO$_4$), filtered and concentrated in vacuo. Purification is effected by flash chromatography on silica gel 60 using CH$_3$OH in CH$_2$Cl$_2$ as eluant to give the pure title acid.

EXAMPLE 5

[1α,2β(Z),3β,4α]-7-[3-(Heptyloxy)bicyclo[2.2.1]hept-2-yl]-5-heptenoic acid

A. (1α,2β,3β,4α)-3-[[[(1,1-Dimethylethyl)dimethylsilyl]oxy]methyl]bicyclo[2.2.1]heptan-2-ol, acetate ester
B. (1α,2β,3β,4α)-3-(Acetyloxy)bicyclo[2.2.1]heptane-2-methanol, trifluoroacetate ester
and
C. (1α,2β,3β,4α)-3-Hydroxybicyclo[2.2.1]heptane-2-methanol To a stirred slurry of 3.34 ml (138 mmol) of 90% H$_2$O$_2$ in 79 ml of dry CH$_2$Cl$_2$ at 0° C. is added dropwise 20.9 ml (149 mmol) of distilled trifluoroacetic anhydride over 20 minutes. This solution is stirred at 0° C. for 55 minutes. To a stirred slurry of 9.9 g (35.5 mmol) of cis-ketone prepared in Example 4 Part C and 37.1 g of dry Na$_2$HPO$_4$ in 99 ml of dry CH$_2$Cl$_2$ at 0° C. is added the above peracid solution dropwise over 80 minutes. The resulting mixture is stirred at 0° C. for 5 hours and 30 minutes and then the solid (Na$_2$HPO$_4$) is removed by filtration. The filter cake is washed with CH$_2$Cl$_2$ (5×120 ml) and filtered. The filtrate is washed with 10% Na$_2$CO$_3$ solution (2×100 ml) and brine (1×200 ml). The organic layer is dried (MgSO$_4$), filtered and concentrated in vacuo. This is chromatographed on silica gel 60 using hexane-ether mixture as eluant to give title A compound, title B acetate and a mixture which contains corresponding title C diol.

D. (1α,2β,3β,4α)-3-(Acetyloxy)bicyclo[2.2.2]heptane-2-methanol

To a stirred solution of 8.75 g (31.3 mmol) of Part B acetate in 100 ml of freshly distilled THF is added 20 ml of H$_2$O and 10 ml of saturated NaHCO$_3$ solution. The reaction mixture is stirred at room temperature for 6 hours and 20 minutes at which time an additional 10 ml of saturated NaHCO$_3$ solution is added. The mixture is stirred for 45 minutes and another 10 ml of saturated NaHCO$_3$ solution is added. The mixture is stirred for an additional 25 minutes and poured into 200 ml of brine. The aqueous layer is saturated with NaCl and extracted with ether (4×250 ml). The combined ether extracts are dried (MgSO$_4$), filtered and concentrated in vacuo to give 5.41 g of crude alcohol. Purification is effected by flash chromatography on silica gel 60 using a CH$_3$OH/CH$_2$Cl$_2$ mixture as eluant to give title alcohol as an oil.

E. (1α,2β,3β,4α)-3-[[(2-Methoxyethoxy)methoxy]methyl]bicyclo[2.2.1]heptan-2-ol, acetate ester To a stirred solution of 2.99 g (16.2 mmol) of Part D alcohol in 25 ml of dry CH$_2$Cl$_2$ under argon is added 5.66 ml (32.5 mmol) of diisopropyl ethyl amine, followed by dropwise addition of 2.78 ml (24.4 mmol) of 2-methoxyethoxymethyl chloride. The reaction mixture is stirred at room temperature for 21 hours and then diluted with 300 ml of CHCl$_3$. The organic layer is washed with 1N HCl solution (2×50 ml), and saturated NaHCO$_3$ solution (1×100 ml). The organic layer is dried (MgSO$_4$), filtered and concentrated in vacuo. Purification is effected by flash chromatography on silica gel 60 using CH$_3$OH in CH$_2$Cl$_2$ as eluant to give title compound as an oil.

F. (1α,2β,3β,4α)-2-(Heptyloxy)-3-[[(2-methoxyethoxy)methoxy]methyl]bicyclo[2.2.1]heptane A mixture of 6.27 g (113 mmol) of powdered KOH in 170 ml of dry xylene is heated to reflux under argon atmosphere and 85 ml of xylene is removed by distillation. To this mixture is added a solution of 3.47 g (12.7 mmol) of Part E compound in 115 ml of dry xylene. The volume of the reaction mixture is reduced 100 ml by distillative removal of xylene. To the reaction mixture is then added a solution of 12.3 g (67.3 mmol) of n-heptyl mesylate in 90 ml of dry xylene. The reaction mixture is refluxed for 3 hours. The cooled reaction mixture is diluted with 200 ml of brine and extracted with EtOAc (5×200 ml). The combined EtOAc extracts are dried (Na$_2$SO$_4$), filtered and concentrated in vacuo. This is chromatographed on 120 g of silica gel 60 using 1:1 hexane-ether as eluant to give 7.08 g of crude ether. Final purification is effected by flash chromatography on silica gel 60 using hexane-ether eluant to give title ether.

G. (1α,2β,3β,4α)-3-Heptyloxybicyclo[2.2.1]heptane-2-methanol

To a stirred solution of 1.88 g (5.76 mmol) of Part F MEM ether in 25 ml of dry $CH_2Cl_2$ under argon at 0° C. is added dropwise 3.28 g (17.3 mmol) of $TiCl_4$. The reaction mixture is stirred for 30 minutes and quenched with 12 ml of concentrated $NH_4OH$ solution. The reaction mixture is diluted with 120 ml of $H_2O$ and extracted with EtOAc (5×100 ml). The combined EtOAc extracts are dried ($MgSO_4$), filtered and concentrated in vacuo. Purification is effected by flash chromatography on 80 g of silica gel 60 using 1% $CH_3OH$ in $CH_2Cl_2$ as eluant to give title heptyl ether alcohol as an oil.

H. (1α,2β,3β,4α)-3-(Heptyloxy)bicyclo[2.2.1]heptane-2-carboxaldehyde

To a stirred mixture of 2.94 g (17.6 mmol) of pyridinium chlorochromate and 0.22 g (2.73 mmol) of NaOAc in 55 ml of dry $CH_2Cl_2$ under argon at room temperature is added rapidly a solution of 1.31 g (5.45 mmol) of Part G heptyl ether alcohol in 16.5 ml of dry $CH_2Cl_2$. The reaction mixture is stirred for 1 hour and 30 minutes and diluted with 72 ml of ether. The organic solution is decanted and the insoluble black residue is washed with ether (2×100 ml) until the precipitate became granular. The combined organic solution is passed through a 3" pad of Florisil which is then washed with ether (3×100 ml). The combined filtrates are concentrated in vacuo to give title aldehyde.

I. (1α,2β,3β,4α)-2-(Heptyloxy)-3-(2-methoxyethenyl)bicyclo[2.2.1]heptane

To a stirred solution of 3.28 g (9.56 mmol) of methoxymethylenetriphenylphosphonium chloride in 45 ml of dry THF under argon in an acetone-ice bath is added 4.97 ml (7.11 mmol) of 1.43M of potassium t-amylate solution dropwise over 10 minutes. To this mixture is added a solution of 1.12 g (4.71 mmol) of Part H aldehyde in 23 ml of dry THF dropwise at 0° C. over 70 minutes. The reaction mixture is stirred at room temperature for 2 hours, cooled in an acetone-ice bath, and then quenched with 20 ml of acetaldehyde. The reaction mixture is diluted with 150 ml of saturated $NH_4Cl$ solution and 50 ml of 1N aqueous HCl solution and extracted with ether (3×270 ml). The combined ether extracts are dried ($MgSO_4$), filtered and concentrated in vacuo. Purification is effected by flash chromatography on 151 g of silica gel 60 using a hexane-ether mixture as eluant to give title vinyl ether as an oil.

J. (1α,2β,3β,4α)-3-(Heptyloxy)bicyclo[2.2.1]heptane-2-acetaldehyde

To a stirred solution of 732 mg (2.76 mmol) of Part I vinyl ether in 7.4 ml of freshly distilled THF under argon is added 29.6 ml of 20% aqueous trifluoroacetic acid solution. The reaction mixture is stirred at room temperature for 3 hours and 10 minutes and then neutralized with solid $NaHCO_3$. The mixture is poured into 100 ml of $H_2O$ and extracted with $CH_2Cl_2$ (4×80 ml). The combined $CH_2Cl_2$ extracts are dried ($MgSO_4$), filtered and concentrated in vacuo to give a colorless oil. This compound is dissolved in 30 ml of benzene and concentrated in vacuo to give title aldehyde as an oil.

K. [1α,2β(Z),3β,4α]-7-[3-(Heptyloxy)bicyclo[2.2.1]hept-2-yl]-5-heptenoic acid, methyl ester To a stirred solution of 1.96 g (4.43 mmol) of carboxybutyltriphenylphosphonium bromide in 35 ml of dry THF under argon at 0° C. is added dropwise 6.23 ml (7.91 mmol) of 1.27M of potassium t-amylate toluene solution. The mixture is stirred at 0° C. for an hour. To this homogeneous burgundy-red solution is added dropwise a solution of 663 mg (2.64 mmol) of Part J cis-aldehyde in 56 ml of dry THF over 80 minutes. The reaction mixture is allowed to warm to room temperature and is stirred for 22 hours and 10 minutes. The reaction mixture is cooled in an ice-bath and quenched with dropwise addition of 10 of glacial acetic acid. The mixture is poured into 100 ml of brine and extracted with EtOAc (4×100 ml). The combined EtOAc extracts are dried ($MgSO_4$), filtered and concentrated in vacuo. The residue is treated with 300 ml of diazomethane solution and excess diazomethane is destroyed by addition of HOAc. The mixture is concentrated in vacuo and chromatographed on silica gel 60 using a hexane-ether mixture as eluant to give 900 mg of an impure mixture of title methyl ester and corresponding carboxylic acid. Purification is effected by flash chromatography on silica gel 60 using a hexane-ether mixture as eluant to give the title methyl ester.

L. [1α,2β(Z),3β,4α]-7-[3-(Heptyloxy)bicyclo[2.2.1]hept-2-yl]-heptenoic acid

To a stirred solution of 346 mg (1.00 mmol) of Part K methyl ester in 54 ml of freshly distilled THF and 9.0 ml of $H_2O$ is added 10.0 ml of 1N aqueous lithium hydroxide solution. The reaction mixture is purged with argon vigorously for 30 minutes and stirred at room temperature for 8 hours and 20 minutes. The reaction mixture is acidified to pH 3 by the addition of 1N aqueous HCl solution and poured into 80 ml of brine. The aqueous layer is saturated with NaCl and extracted with EtOAc (4×100 ml). The combined EtOAc extracts are dried ($MgSO_4$), filtered and concentrated in vacuo. Purification is effected by flash chromatography on silica gel 60 using $CH_3OH$ in $CH_2Cl_2$ as eluant to give the pure title acid.

EXAMPLE 6

[1α,2β(Z),3α,4α]-7-[3-(Heptylthio)bicyclo[2.2.1]-hept-2-yl]-5-heptenoic acid

A. (1α,2β,3β,4α)-3-Hydroxybicyclo[2.2.1]heptane-2-methanol

A flask containing 250 ml of dry $CH_2Cl_2$ is cooled in an ice bath. To this is added 8.8 ml (364 mmol) of 90% $H_2O_2$. To this stirred slurry is added dropwise 58 ml (411 mmol) of trifluoroacetic anhydride over 40 minutes. During this time the pot temperature varies between 2°-7° C. The solution is stirred for an additional 25 minutes at 0° C.

A solution of 8.0 g (47 mmol) of the Example 4, Part B hemiketal in 280 ml of $CH_2Cl_2$ is cooled to 0° C. and then 96 g (676 mmol) of anhydrous $Na_2HPO_4$ is added. To this mechanically stirred slurry is added the above peracid solution in 10 ml portions over 35 minutes. The reaction is stirred at 0°→2° C. for an additional 18 hours and is then allowed to warm to room temperature and stirred for an additional 48 hours. The reaction mixture is then diluted with 100 ml $CH_2Cl_2$ and the solids are removed by filtration. The filter cake is washed with ~200 ml of ether and enough $CH_2Cl_2$ to afford ~1400 ml of filtrate. The filtrate is concentrated in vacuo to afford 18 g of crude oxidation product in the form of a colorless oil.

A slurry of 4.6 g (121 mmol) of $LiAlH_4$ in 150 ml of ether under Ar is cooled in an ice bath. To this stirred slurry is added dropwise a solution of 18 g of crude oxidation product in 70 ml of ether. After 70 minutes, an additional 4.1 g (108 mmol) of LiAlH$_4$ is added. Thirty minutes later, the addition is complete and the flask is warmed to room temperature. After being stirred for 2.5 hours, the reaction mixture is diluted with 200 ml ether and then cooled in an ice bath. To this vigorously stirred mixture is added 8.5 ml of H$_2$O dropwise over 30 minutes, followed by the sequential addition of 8.5 ml of 15% NaOH and 25.5 ml H$_2$O. The mixture is diluted with 100 ml EtOAc and filtered to remove solids. The filter cake is resuspended in 10% CH$_3$OH in EtOAc (350 ml), stirred, and filtered. This washing procedure is repeated twice. The combined filtrates are concentrated in vacuo to afford 10.5 g of crude title diol. A 9.9 g portion of this material is chromatographed on 225 g of silica gel using a CH$_3$OH/CH$_2$Cl$_2$ mixture as eluants. This affords title diol, a mixture of title dioland (1α,2β,3β,4α)-bicyclo[2.2.1]heptane-2,3-dimethanol and the monoacetate (1α,2β,3β,4α)-3-(acetyloxy)bicyclo[2.2.1]heptane-2-methanol.

B. (1α,2β,3β,4α)-3-Hydroxybicyclo[2.2.1]heptane-2-methanol, 4-methylbenzenesulfonate ester A solution of 5.5 g (38.2 mmol) of the part A diol, 20 ml of pyridine, and 10 ml of dry CH$_2$Cl$_2$ is cooled to −20° C. under argon. To this stirred solution is added dropwise a solution of 8.23 g (43.2 mmol) of recrystalized TsCl in 25 ml of CH$_2$Cl$_2$ over a period of 30 minutes. The reaction mixture is stirred at −20° C. for 2 hours and then the flask is placed in the refrigerator (3°–5° C.) for 4 days. The flask is then allowed to warm to room temperature with stirring. The reaction mixture is partitioned between 300 ml of ether and 200 ml of 1N HCl. The organic layer is washed with 100 ml of 1N HCl. The combined aqueous layers are then extracted with 150 ml of ether. The combined organic layers are dried over MgSO$_4$, filtered and concentrated in vacuo to give 11.7 g of white solid. This solid is stirred with approximately 75 ml of ether and then 25 ml of hexane is added. After chilling this mixture in the refrigerator for several hours, the white precipitate is collected and dried in vacuo to give title B tosylate.

C. (1α,2β,3β,4α)-3-[(Tetrahydro-2H-pyran-2-yl)oxy]bicyclo[2.2.1]heptane-2-methanol, 4-methylbenzenesulfonate ester A solution of 8.2 g (27.5 mmol) of the part B tosylate in 130 ml of dry CH$_2$Cl$_2$ is cooled to 0° C. To this rapidly stirred solution is added 0.10 g of p-TsOH followed by dropwise addition of 4.0 ml (43.9 mmol) of dihydropyran. The flask is covered with foil and maintained at 0° C. After stirring for 4 hours, the reaction mixture is added to 100 ml of saturated NaHCO$_3$ solution. The aqueous layer is extracted twice with 100 ml of CH$_2$Cl$_2$. The combined CH$_2$Cl$_2$ layers are dried over MgSO$_4$, filtered and concentrated in vacuo to afford the crude product.

This was chromatographed on 180 g of silica gel using hexane-ether mixtures as eluant to afford the title C THP ether.

D. (1α,2β,3β,4α)-3-[(Tetrahydro-2H-pyran-2-yl)oxy]bicyclo[2.2.1]heptane-2-acetonitrile To a stirred solution of 7.0 g (18.3 mmol) of the part C THP ether in 70 ml of dry DMSO is added 5.95 g (121 mmol) of NaCN (powdered) and 0.12 g of NaHCO$_3$. This mixture is placed in a 95° C. oil bath for 4 hours. On cooling, the reaction mixture is partitioned between 500 ml of brine and 400 ml of ether. The aqueous layer is then extracted with three 400 ml portions of ether. The combined ether extracts are dried over MgSO$_4$, filtered and concentrated in vacuo to afford 5.4 g of crude product. Flash chromatography on silica gel using ether-hexane mixtures as eluant gives title D nitrile.

E. (1α,2β,3β,4α)-3-[(Tetrahydro-2H-pyran-2-yl)oxy]bicyclo[2.2.1]heptane-2-acetaldehyde A solution of 4.2 g (17.7 mmol) of the Part D nitrile in 50 ml of dry toluene is cooled to −20° C. To this stirred solution is added dropwise 30 ml of 25% DIBAL in toluene (44.6 mmol) over a period of 10 minutes. The bath temperature is maintained at −20°→15° C. for 3½ hours. The reaction is then quenched at −20° C. by the addition of 30 ml of acetone, and then diluted with 250 ml of toluene. To this is added 100 g of silica gel followed by the dropwise addition of 10 ml of H$_2$O and 4.0 ml of glacial HOAc. This slurry is stirred vigorously for 45 minutes at room temperature. The silica gel is removed and the cake washed with three 300 ml portions of acetone. The combined filtrates are concentrated in vacuo, redissolved in 100 ml of ether and washed with 80 ml of half-saturated NaCl solution. The aqueous layer is back-extracted with 100 ml of ether. The combined ether layers are dried over Na$_2$SO$_4$, filtered and concentrated in vacuo to afford title E aldehyde.

F. (1α,2β(Z),3β,4α)-7-(3-Hydroxybicyclo[2.2.1]hept-2-yl)-5-heptenoic acid, methyl ester A slurry of 51.75 g (117 mmol) of carboxybutyltriphenylphosphonium bromide in 400 ml of THF is cooled in an ice bath under argon. To this stirred slurry is added dropwise 60 ml (84 mmol) of 1.4M KOt-amylate/toluene over a period of 48 minutes. At this point, the reaction mixture is allowed to warm to room temperature. The ylid solution is stirred at room temperature for 5½ hours at which time the addition of a solution of 3.7 g (15.4 mmol) of crude Part E aldehyde in 100 ml of THF is begun. The addition is complete after 55 minutes, and the resulting mixture is stirred at room temperature overnight. The mixture is cooled in an ice bath and quenched by the addition of a solution of 25 ml HOAc in 25 ml of toluene, followed by dilution with an additional 300 ml of toluene. The precipitate is removed by filtration and the filtrate is partitioned between 800 ml of half-saturated NaCl and 500 ml EtOAc (pH of aqueous layer is 3.5). The aqueous layer is then extracted with 3×500 ml of EtOAc. The combined organic layers are dried over MgSO$_4$, filtered, and concentrated in vacuo to give 12.6 g of crude product. This is triturated with iPr$_2$O/hexane. The filtrate is concentrated in vacuo to afford 8.8 g of crude acid. This is esterified with excess CH$_2$N$_2$ at 0° C. The resultant ester was chromatographed on silica gel using MeOH in CH$_2$Cl$_2$ as eluant, giving title F heptenoic acid ester.

G. [1α,2β(Z),3β,4α]-7-(3-Hydroxybicyclo[2.2.1]hept-2-yl)-5-heptenoic acid, methyl ester To a solution of 3.8 g (11.2 mmol) of the Part F heptenoic acid ester in 40 ml of MeOH is added 600 mg of crushed, dried Amberlyst 15 resin. This mixture is stirred vigorously for 4 hours at room temperature. It is then diluted with 100 ml of ether and filtered through a short pad of Celite. The filter cake is washed thoroughly with ether. The combined filtrates are concentrated in vacuo, combined and chromatographed on silica gel using MeOH/CH$_2$Cl$_2$ mixture as eluant. This affords title alcohol ester.

H. [1α,2β(Z),3α,4α]-7-[3-(Acetylthio)bicyclo[2.2.1]hept-2-yl]-5-heptenoic acid, methyl ester Diisopropyl azo dicarboxylate (DIAD) (1.2 ml, 1.23 g, 6.1 mmol) is added dropwise over 1 minute to a stirred solution of triphenylphosphine (1.56 g, 5.9 mmol) in 15 ml THF at 0° under Ar. This mixture is stirred 30 minutes. To this stirred solution is added dropwise a solution of 520 mg (2.06 mmol) of the title G alcohol ester and 0.75 ml (0.80 g, 10.5 mmol) of thiolacetic acid and 3 ml THF, over 10 minutes. This mixture is allowed to stir overnight.

The reaction mixture is concentrated in vacuo, the residue triturated with hexane:ether (1:1), and the solid removed by filtration. The filtrate is concentrated in vacuo and the resulting semi-solid is purified by chromatography on silica gel using hexane:ether mixtures as eluant. This gives the title thioacetate.

I. [1α,2β(Z),3α,4α]-7-[3-(Heptylthio)bicyclo[2.2.1]hept-2-yl]-5-heptenoic acid, methyl ester and

[1α,2β(Z),3α,4α]-7-[3-(Heptylthio)bicyclo[2.2.1]hept-2-yl]-5-heptenoic acid, heptyl ester A slurry of 10 ml of xylene and 500 mg of powdered KOH is heated to reflux. A solution of 210 mg of the title H thioacetate (0.68 mmol) and 0.7 ml of n-heptyl bromide in 2 ml xylene is added and the mixture is refluxed 3.5 hours. An additional 1.1 ml of heptyl bromide is then added and the mixture is refluxed an additional 1.25 hour.

On cooling, the reaction mixture is partitioned between 25 ml each of saturated NaCl and ether. The aqueous layer is acidified to pH 4 by careful addition of 6N HCl, and extracted with ether. All ether extracts are combined and treated with ethereal diazomethane to convert any free acid present to the methyl ester. Acetic acid is added to destroy any excess diazomethane. The organic solution is then washed with saturated NaHCO$_3$, saturated NaCl and dried over MgSO$_4$. It is filtered and concentrated in vacuo. Chromatography of the resulting oil on silica gel using hexane:ether mixtures as eluant gives a mixture of the title methyl and heptyl esters in good yield.

J. [1α,2β(Z),3α,4α]-7-[3-(Hexylthio)bicyclo[2.2.1]hept-2-yl]-5-heptenoic acid

To a stirred solution of 126 mg (0.27 mmol) of the part I methyl and heptyl esters in 12.9 ml of freshly distilled THF is added 2.5 ml H$_2$O and 2.9 ml of N aqueous LiOH. The reaction mixture is purged with argon and stirred at room temperature for 8.5 hours. The reaction mixture is acidified to pH 3 by the addition of 1N HCl and poured into 70 ml brine. The resulting solution is saturated with NaCl and extracted with ethyl acetate (4×100 ml). The combined ethyl acetate extracts are dried (Na$_2$SO$_4$), filtered and concentrated in vacuo to give a crude oil, which is purified by flash chromatography on silica gel 60 using hexane-ether mixtures as eluant to give title acid.

EXAMPLE 7

[1α,2β(Z),3β,4α]-7-[3-(Heptylthio)bicyclo[2.2.1]hept-2-yl]-5-heptenoic acid

A. [1α,2β(Z),3β,4α]-7-(3-Oxobicyclo[2.2.1]hept-2-yl)-5-heptenoic acid, methyl ester To a solution of 1.12 g (8.86 mmol) of oxalyl chloride in 15 ml of dry CH$_2$Cl$_2$ at −78° C. under argon atmosphere is added 1.38 g (17.7 mmol) of dry DMSO over 10 minutes. To this mixture is added a solution of 1.50 g (5.91 mmol) of the Example 6, Part G alcohol in 30 ml of dry CH$_2$Cl$_2$ dropwise over 20 minutes. The reaction mixture is stirred for 65 minutes and then 4.56 g (45.1 mmol) of triethyl amine is added dropwise. The resulting mixture is allowed to warm to room temperature and stirred for 35 minutes. The mixture is then diluted with 500 g of ether and washed with 1N aqueous HCl solution (3×125 ml), saturated NaHCO$_3$ solution (1×125 ml) and brine (1×200 ml). The solution is dried over anhydrous MgSO$_4$, filtered and concentrated in vacuo to give title ketone.

B. [1α,2β(Z),3α,4α]-7-(3-Hydroxybicyclo[2.2.1]hept-2-yl)-5-heptenoic acid, methyl ester To a stirred solution of 0.23 g (6.13 mmol) of NaBH$_4$ in 80 ml CH$_3$OH at 0° C. under argon is added a solution of 1.49 (5.91 mmol) of Part A ketone in 80 ml of CH$_3$OH dropwise. The reaction mixture is stirred for 65 minutes and then quenched by the addition of 3 ml of acetone. This mixture is concentrated in vacuo to about 20 ml and diluted with 300 ml of ether. The resulting solution is washed once with 150 ml of 1N aqueous HCl solution. The aqueous layer is saturated with NaCl and extracted with ether (2×300 ml). The combined ether extracts are dried over anhydrous Na$_2$SO$_4$, filtered, concentrated in vacuo, and chromatographed on silica gel 60 using ether-hexane mixtures as eluant to give title endo-alcohol.

C. [1α,2β(Z),3α,4α]-7-[3-[(Methylsulfonyl)oxy]bicyclo[2.2.1]hept-2-yl]-5-heptenoic acid, methyl ester To a stirred solution of 900 mg (3.54 mmol) of Part B endo-alcohol in 18 ml of dry pyridine at 0° C. under argon is added a solution of 1.63 g (14.2 mmol) of mesyl chloride in 18 ml of dry CH$_2$Cl$_2$. This mixture is allowed to warm to room temperature and stirred for 7 hours. The mixture is diluted with 700 ml of ether and washed with 1N HCl (2×180 ml), saturated NaHCO$_3$ solution (1×150 ml) and brine (1×200 ml). The ether solution is dried over anhydrous Na$_2$SO$_4$, filtered and concentrated in vacuo. Purification is effected by flash chromatography on silica gel 60 using hexane-ether mixtures as eluant to give mesylate.

D. [1α,2β(Z),3β,4α]-7-[3-(Heptylthio)bicyclo[2.2.1]hept-2-yl]-5-heptenoic acid, methyl ester To a stirred solution of 134 mg (1.05 mmol) of potassium t-butoxide in 1 ml of dry THF under argon is added 0.36 ml (2.11 mmol) of heptyl mercaptan. To this mixture is added a solution of 100 mg (0.30 mmol) of Part C mesylate in 1 ml of dry THF. The reaction mixture is diluted with 2 ml of dry DMSO and heated at 95° C. for 6 hours and 20 minutes. The cooled reaction mixture is diluted with 30 ml of half-saturated NaCl solution and extracted with 40 ml of ether. The aqueous layer is acidified to pH 4.5 by the addition of 1N aqueous HCl solution and extracted with ether (3×40 ml). The combined ether extracts are washed with 20 ml of water, dried (MgSO$_4$), filtered and concentrated in vacuo. The residue is treated with ethereal diazomethane at room temperature and the excess diazomethane is destroyed by the addition of glacial HOAc. Concentration in vacuo gives the crude product. Purification is effected by flash chromatography on silica gel 60. Hexane-ether mixtures are used for elution. This gives the title thioether.

E. [1α,2β(Z),3β,4α]-7-[3-(Heptylthio)bicyclo[2.2.1]hept-2-yl]-5-heptenoic acid

To a stirred solution of 101 mg (0.27 mmol) of Part D ester in 12.9 ml of freshly distilled THF is added 2.5 ml of H$_2$O and 2.9 ml of 1N aqueous lithium hydroxide solution. The reaction mixture is purged with argon vigorously for 15 minutes and stirred at room temperature for 8 hours and 30 minutes. Another batch of 25 mg of methyl ester is hydrolyzed separately in the same manner and then combined for work-up. The combined reaction mixtures are acidified to pH 3 by the addition of 1N aqueous HCl solution and poured into 70 ml of brine. The resulting solution is saturated with NaCl and extracted with EtOAc (4×100 ml). The combined EtOAc extracts are dried ($Na_2SO_4$), filtered and concentrated in vacuo to give 200 mg of crude product as an oil. Purification is effected by flash chromatography on silica gel 60 using hexane-ether mixtures as eluant to give title acid.

EXAMPLE 8

[1α,2β(Z),3β,4α]-7-[3-(Methyloxy)methyl]bicyclo[2.2.1]hept-2-yl]-5-heptenoic acid Following the procedure of Example 1 except substituting methyl methanesulfonate for n-hexyl methanesulfonate, the title compound is obtained.

EXAMPLE 9

(1β,2α,3α,4β)-7-[3-(Butyloxy)methyl]bicyclo[2.2.1]hept-2-yl]-5-heptanoic acid

Following the procedure of Examples 1 and 2 except substituting n-butyl methanesulfonate for n-hexyl methanesulfonate, the title compound is obtained.

EXAMPLE 10

[1β,2α(Z),3α,4β]-7-[3-[(Octyloxy)methyl]bicyclo[2.2.1]hept-2-yl]-5-heptenoic acid Following the procedure of Example 1 except substituting n-octyl methanesulfonate for n-hexyl methanesulfonate, the title compound is obtained.

EXAMPLE 11

[1β,2α(Z),3α,4β]-7-[3-[(Phenyloxy)methyl]bicyclo[2.2.1]hept-2-yl]-5-heptenoic acid (a) Phenol (1 mmol) is added to a solution of triphenylphosphine (1 mmol), diethylazodicarboxylate (1 mmol) and title G alcohol from Example 1 (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give [1β,2α(Z),3α,4β]-7-[3-[(phenyloxy)methyl]bicyclo[2.2.1]hept-2-yl]-5-heptenoic acid, methyl ester.

(b) Following the procedure as set out in Example 1 Part J, the ester from part (a) is converted to the title compound.

EXAMPLE 12

[1β,2α(Z),3α,4β]-7-[3-[(Ethyloxy)methyl]bicyclo[2.2.1]hept-2-yl]-5-heptenoic acid Following the procedure of Example 1 except substituting ethyl methanesulfonate for n-hexylmethane sulfonate, the title compound is obtained.

EXAMPLE 13

(1β,2α,3α,4β)-7-[3-[(Phenyloxy)methyl]bicyclo[2.2.1]hept-2-yl]-5-heptanoic acid

Following the procedure of Examples 11 and 2 except substituting the Example 11 compound for the Example 1 compound in Example 2, the title compound is obtained.

EXAMPLE 14

[1β,2α(Z),3α,4β]-7-[3-[(Benzyloxy)methyl]bicyclo[2.2.1]hept-2-yl]-5-heptenoic acid Following the procedure of Example 1 except substituting benzyl methane sulfonate for n-hexylmethane sulfonate, the title compound is obtained.

EXAMPLE 15

(1β,2α,3α,4β)-7-[3-[(Benzyloxy)methyl]bicyclo[2.2.1]hept-2-yl]heptanoic acid

Following the procedure of Example 2 except substituting the Example 14 acid for the Example 1 acid, the title compound is obtained.

EXAMPLE 16

[1β,2α(Z),3α,4β]-7-[3-[(Cyclohexyloxy)methyl]bicyclo[2.2.1]hept-2-yl]-5-heptenoic acid Following the procedure of Example 1 except substituting cyclohexyl methanesulfonate for n-hexyl methanesulfonate, the title compound is obtained.

EXAMPLE 17

[1β,2α(Z),3α,4β]-7-[3-[(Cyclopentyloxy)methyl]bicyclo[2.2.1]hept-2-yl]-5-heptenoic acid Following the procedure of Example 1 except substituting cyclopentyl methanesulfonate for n-hexyl methanesulfonate, the title compound is obtained.

EXAMPLE 18

(1β,2α,3α,4β)-7-[3-[(Cyclohexyloxy)methyl]bicyclo[2.2.1]hept-2-yl]-5-heptanoic acid Following the procedure of Example 2 except substituting the Examples 16 acid for the Example 1 acid, the title compound is obtained.

EXAMPLE 19

[1β,2α(Z),3α,4β]-7-[3-[2-(Hexyloxy)ethyl]bicyclo[2.2.1]hept-2-yl]-5-heptenoic acid A. [1β,2α(Z),3α,4β]-7-[[3-(2-Oxo)ethyl]-bicyclo[2.2.1]hept-2-yl]-5-heptenoic acid, methyl ester Into a dry 100 ml round bottom 3-necked flask containing a stir bar is added dried 12.9 g (37.7 mmoles) methoxymethyltriphenylphosphonium chloride (($C_6H_5$)$_3P^+$—$CH_2OCH_3Cl^-$) and 235 ml distilled toluene (stored over molecular sieves). The resulting suspension is stirred in an ice-bath, under argon, until cold and then a 1.55M solution of 18.3 ml (28.3 mmol) of potassium t-amylate in toluene was added dropwise. A bright red solution formed which is stirred at 0° C. for an additional 35 minutes. Thereafter, a solution of 4.97 g (18.8 mmol) [1β,2α(Z),3α,4β]-7-(3-formyl)bicyclo[2.2.1]hept-2-yl]-5-heptenoic acid, methyl ester in 60 ml toluene is added by means of a dropping funnel over a 35 minute period with the ice-bath still in place. The reaction is then quenched by addition of 2.3 g (39 mmol) acetic acid in 5 ml ether. The reaction mixture is immediately poured into 200 ml saturated $NH_4Cl$, and extracted with ether (4×200 ml). The combined ether phases are washed with NaCl saturated solution, and dried ($MgSO_4$) and concentrated to yield a yellow oil in a white crystalline solid (phosphine oxide). The white solid is triturated with EtOAc and the mother liquor is purified by chromatography on an LPS-1 silica column. The fractions obtained are (A) [1β,2α(Z),3α,4β]-7-[[3-

(2-oxo)ethyl]bicyclo[2.2.1]-hept-2-yl]-5-heptenoic acid, methyl ester, (B) [1β,2α(Z),3α,4β]-7-[3-(2-methoxy)ethendiyl]bicyclo[2.2.1]hept-2-yl]-5-heptenoic acid, methyl ester, and (C) [1β, 2α(Z),3α,4β]-7-[[3-(2,2-dimethoxy)ethyl]bicyclo[2.2.1]hept-2-yl]-5-heptenoic acid, methyl ester.

Compounds (B) and (C) are each treated with trifluoroacetic acid to convert each to compound (A).

B. [1β,2α(Z),3α,4β]-7-[3-(2-Hydroxyethyl)bicyclo[2.2.1]hept-2-yl]-5-heptenoic acid, methyl ester The aldehyde (1.4 g, 5 mmol) from part A in methanol (50 ml) is treated with NaBH₄ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO₃, saturated NaCl and dried (MgSO₄). The ether is evaporated to yield the title B compound.

C. [1β,2α(Z),3α,4β]-7-[3-(2-Hexyloxy)ethyl]bicyclo[2.2.1]hept-2-yl]-5-heptenoic acid Following the procedure of Examples 1 and 2 except substituting the above part B alcohol for the alcohol used in Example 1, the title compound is obtained.

EXAMPLE 20

(1β,2α,3α,4β)-7-[3-[2-(Hexyloxy)ethyl]bicyclo[2.2.1-]hept-2-yl]heptanoic acid

Following the procedure of Example 19 except substituting (1β,2α,3α,4β)-7-[(3-formyl)bicyclo[2.2.1]hept-2-yl]-5-heptanoic acid, methyl ester for [1β,2α(Z)-,3α,4β]-7-[(3-formyl)bicyclo[2.2.1]-hept-2-yl]-5-heptenoic acid, methyl ester, the title compound is obtained.

EXAMPLE 21

(1β,2α,3α,4β)-7-[3-[2-(Phenyloxy)ethyl]bicyclo[2.2.1-]hept-2-yl]heptanoic acid

Following the procedure of Examples 11, 20 and 2 except substituting (1β,2α,3α,4β)-7-[3-[2-(hydroxy)ethyl]bicyclo[2.2.1]hept-2-yl]heptanoic acid, methyl ester for [1β,2α(Z),3α,4β]-7-[3-(hydroxymethyl)bicyclo[2.2.1]hept-2-yl]-5-heptenoic acid, methyl ester, the title compound is obtained.

EXAMPLE 22

1β,2α(Z),3α,4β]-7-[3-82-(Benzyloxy)ethyl]bicyclo[2.2.1]hept-2-yl]-5-heptenoic acid Following the procedure of Example 19 except substituting benzyl methanesulfonate for n-hexylmethane sulfonate, the title compound is obtained.

EXAMPLE 23

[1β,2α(Z),3α,4β]-7-[3-[2-(Cyclopentyloxy)ethyl]bicyclo[2.2.1]hept-2-yl]-5-heptenoic acid Following the procedure of Example 19 except substituting cyclopentyl methanesulfonate for n-hexyl methanesulfonate, the title compound is obtained.

EXAMPLE 24

[1β,2α(Z),3α,4β]-7-[3-[2-(Cyclohexyloxy)ethyl]bicyclo[2.2.1]hept-2-yl]-5-heptenoic acid Following the procedure of Example 19 except substituting cyclohexyl methanesulfonate for n-hexyl methanesulfonate, the title compound is obtained.

EXAMPLE 25

[1β,2α(Z),3α,4β]-7-[3-[4-(Hexyloxy)butyl]bicyclo[2.2.1]hept-2-yl]-5-heptenoic acid A. [1β,2α(Z),3α,4β]-7-[[3-(3-Oxo)propyl]bicyclo[2.2.1]hept-2-yl]-5-heptenoic acid, mehyl ester Following the procedure of Example 19, part A except substituting [1β,2α(Z),3α,4β]-7-[[3-(2-oxo)ethyl]bicyclo[2.2.1]hept-2-yl]-5-heptenoic acid, methyl ester for [1β,2α(Z),3α,4β]-7-[[3-formyl]bicyclo[2.2.1]hept-2-yl]-5-heptenoic acid, methyl ester, the title A compound is obtained.

B. [1β,2α(Z),3α,4β]-7-[3-(4-Oxo)butylbicyclo[2.2.1]hept-2-yl]-5-heptenoic acid, methyl ester Following the procedure of Example 19, part A, except substituting the aldehyde from part A above for [1β,2α(Z),3α,4β]-7-[[3-formyl]bicyclo[2.2.1]hept-2-yl]-5-heptenoic acid, methyl ester, the title B compound is obtained.

C. [1β,2α(Z),3α,4β]-7-[3-(4-Hydroxybutyl)bicyclo[2.2.1]hept-2-yl]-5-hepenoic acid, methyl ester Following the procedure of Example 19, part B, except substituting the title B aldehyde for [1β,2α(Z)-,3α,4β]-7-[[3-(2-oxoethyl]bicyclo[2.2.1]-hept-2-yl]-5-heptenoic acid, methyl ester, the title C aldohol is obtained.

D. [1β,2α(Z),3α,4β]-7-[3-[4-(Hexyloxy)butyl]bicyclo[2.2.1]hept-2-yl]-5-heptenoic acid Following the procedure of Example 1, except substituting the above part C alcohol for the alcohol used in Example 1, the title compound is obtained.

EXAMPLE 26

[1β,2α(Z),3α,4β]-7-[3-[4-(Cyclohexyloxy)butyl]bicyclo[2.2.1]hept-2-yl]-5-heptenoic acid Following the procedure of Example 25 except substituting cyclohexyl methanesulfonate for n-hexyl methanesulfonate, the title compound is obtained.

EXAMPLE 27

[1β,2α(Z),3α,4β]-7-[3-[4-(Phenyloxy)butyl]bicyclo[2.2.1]hept-2-yl]-5-heptenoic acid Following the procedure of Examples 11 and 25 except substituting [1β,2α(Z),3α,4β]-7-[3-(4-hydroxybutyl)bicyclo[2.2.1]hept-2-yl]-5-heptenoic acid, methyl ester for [1β,2α(Z),3α,4β]-7-[3-(hydroxymethyl)bicyclo[2.2.1]hept-2-yl]-5-heptenoic acid, methyl ester, the title compound is obtained.

EXAMPLE 28

[1β,2α(Z),3α,4β]-7-[3-[4-(Benzyloxy)butyl]bicyclo[2.2.1]hept-2-yl]-5-heptenoic acid Following the procedure of Example 25 except substituting benzyl methanesulfonate for n-hexyl methanesulfonate, the title compound is obtained.

EXAMPLE 29

Tris(hydroxymethyl)aminomethane salt of [1β,2α(Z),3α,4β]-7-[3-[(Hexyloxy)methyl]bicyclo[2.2.1]-hept-2-yl]-5-heptenoic acid A solution of the compound formed in Example 1 in methanol is treated with an equivalent amount of tri(hydroxymethyl)aminomethane. The solvent is removed by evaporation to yield the title compound.

EXAMPLE 30

[1β,2α(Z),3α,4β]-7-[3-[(Methylthio)methyl]bicyclo[2.2.1]hept-2-yl]-5-heptenoic acid Following the procedure of Example 3 except substituting methyl mercaptan for 1-hexanethiol, the title compound is obtained.

EXAMPLE 31

[1β,2α(Z),3α,4β]-7-[3-[(Propylthio)methyl]bicyclo[2.2.1]hept-2-yl]-5-heptenoic acid Following the procedure of Example 3 except substituting propylmercaptan for 1-hexanethiol, the title compound is obtained.

EXAMPLE 32

(1β,2α,3α,4β)-7-[3-(Butylthio)methyl]bicyclo[2.2.1]hept-2-yl]heptanoic acid

Following the procedure of Examples 3 and 2 except substituting butylmercaptan for 1-hexanethiol, the title compound is obtained.

EXAMPLE 33

[1β,2α(Z),3α,4β]-7-[3-[(Octylthio)methyl]bicyclo[2.2.1]hept-2-yl]-5-heptenoic acid Following the procedure of Example 3 except substituting 1-octanethiol for 1-hexanethiol, the title compound is obtained.

EXAMPLE 34

[1β,α(Z),3α,4β]-7-[3-[(Phenylthio)methyl]bicyclo[2.2.1]hept-2-yl]-5-heptenoic acid Following the procedure of Example 3 except substituting phenylmercaptan for 1-hexanethiol, the title compound is obtained.

EXAMPLE 35

(1β,2α,3α,4β)-7-[3-[(Phenylthio)methyl]bicyclo[2.2.1]hept-2-yl]heptanoic acid

Following the procedure of Examples 3 and 2 except substituting phenylmercaptan for 1-hexanethiol, the title compound is obtained.

EXAMPLE 36

[1β,2α(Z),3α,4β]-7-[3-[(Ethylthio)methyl]bicyclo[2.2.1]hept-2-yl]-5-heptenoic acid Following the procedure of Example 3 except substituting ethylmercaptan for 1-hexanethiol, the title compound is obtained.

EXAMPLE 37

[1β,2α(Z),3α,4β]-[3-[(Benzylthio)methyl]bicyclo[2.2.1]hept-2-yl]-5-heptenoic acid Following the procedure of Example 3 except substituting benzylmercaptan for 1-hexanethiol, the title product is obtained.

EXAMPLE 38

(1β,2α,3α,4β)-7-[3-[(Benzylthio)methyl]bicyclo[2.2.1]hept-2-yl]heptanoic acid

Following the procedure of Examples 37, 3 and 2 except substituting Example 1 part G olefin for the acid used in Example 2, the title compound is obtained.

EXAMPLE 39

[1β,2α(Z),3α,4β]-7-[3-[(Cyclohexylthio)methyl]bicyclo[2.2.1]hept-2-yl]-5-heptenoic acid Following the procedure of Example 3 except substituting cyclohexylmercaptan for 1-hexanethiol, the title compound is obtained.

EXAMPLE 40

(1β,2α,3α,4β)-7-[3-[(Cyclohexylthio)methyl]bicyclo[2.2.1]hept-2-yl]heptanoic acid Following the procedure of Examples 3 and 2 except substituting cyclohexylmercaptan for 1-hexanethiol, the title product is obtained.

EXAMPLE 41

[1β,2α(Z),3α,4β]-7-[3-[2-(Hexylthio)ethyl]bicyclo[2.2.1]hept-2-yl]-5-heptenoic acid Following the procedure of Examples 19 and 3 except substituting the Example 19 part B alcohol for the alcohol used in Example 3, the title compound is obtained.

EXAMPLE 42

(1β,2α,3α,4β)-7-[3-[2-(Hexylthio)ethyl]bicyclo[2.2.1]hept-2-yl]heptanoic acid

Following the procedure of Examples 19, 20 and 3 except substituting Example 19 Part B alcohol for the alcohol used in Example 3 Part A, the title compound is obtained.

EXAMPLE 43

[1β,2α(Z),3α,4β]-7-[3-[2-(Phenylthio)ethyl]bicyclo[2.2.1]hept-2-yl]-5-heptenoic acid Following the procedure of Examples 19 and 20 except substituting the Example 19 Part B alcohol for the alcohol used in Example 3, Part A and substituting phenylmercaptan for 1-hexanethiol (of Example 3), the title compound is obtained.

EXAMPLE 44

(1β,2α,3α,4β)-7-[3-[2-(Phenylthio)ethyl]bicyclo[2.2.1]hept-2-yl]-5-heptanoic acid Following the procedure of Examples 19, 20 and 3 except substituting the Example 19 Part B alcohol for the alcohol used in Example 3, Part A and substituting phenylmercaptan for 1-hexanethiol (of Example 3), the title compound is obtained.

EXAMPLE 45

[1β,2α(Z),3α,4β]-7-[3-[2-(Benzylthio)ethyl]bicyclo[2.2.1]hept-2-yl]-5-heptenoic acid Following the procedure of Examples 19 and 3 except substituting the Example 19 Part B alcohol for the alcohol used in Example 3, Part A and substituting benzylmercaptan for 1-hexanethiol (of Example 3), the title compound is obtained.

EXAMPLE 46

[1β,2α(Z),3α,4β]-7-[3-[2-(Cyclopentylthio)ethyl]bicyclo[2.2.1]hept-2-yl]-5-heptenoic acid Following the procedure of Examples 19 and 3 except substituting the Example 19B alcohol for the alcohol used in Example 3, Part A and substituting cyclopentylmercaptan for 1-hexanethiol (of Example 3), the title compound is obtained.

EXAMPLE 47

[1β,2α(Z),3α,4β]-7-[3-[2-(Cyclohexylthio)ethyl]-bicyclo[2.2.1]hept-2-yl]-5-heptenoic acid Following the procedure of Example 20 except substituting the Example 19B alcohol for the alcohol used in Example 3, Part A and substituting cyclohexylmercaptan for 1-hexanethiol (of Example 3), the title product is obtained.

EXAMPLE 48

[1β,2α(Z),3α,4β]-7-[3-[4-(Hexylthio)butyl]bicyclo[2.2.1]hept-2-yl]-5-heptenoic acid Following the procedure of Examples 25 and 3 except substituting the Example 25 part C alcohol for the alcohol used in Example 3, the title compound is obtained.

EXAMPLE 49

[1β,2α(Z),3α,4β]-7-[3-[4-(Cyclohexylthio)butyl]bicyclo[2.2.1]hept-2-yl]-5-heptenoic acid Following the procedure of Example 48 except substituting cyclohexylmercaptan for 1-hexanethiol, the title compound is obtained.

EXAMPLE 50

[1β,2α(Z),3α,4β]-7-[3-[4-(Phenylthio)butyl]bicyclo[2.2.1]hept-2-yl]-5-heptenoic acid Following the procedure of Example 48 except substituting phenylmercaptan for 1-hexanethiol, the title compound is obtained.

EXAMPLE 51

[1β,2α(Z),3α,4β]-7-[3-[4-(Benzylthio)butyl]bicyclo[2.2.1]hept-2-yl]-5-heptenoic acid Following the procedure of Example 48 except substituting benzylmercaptan for 1-hexanethiol, the title compound is obtained.

EXAMPLES 52, 53 AND 54

[1β,2α(Z),3α,4β]-7-[3-[(Hexylsulfinyl)methyl]bicyclo[2.2.1]hept-2-yl]-5-heptenoic acid, methyl ester (fast moving isomer) (Example 52)

[1β,2α(Z),3α,4β]-7-[3-[(Hexylsulfinyl)methyl]bicyclo[2.2.1]hept-2-yl]-5-heptenoic acid, methyl ester (slow moving isomer) (Example 53)

and

[1β,2α(Z),3α,4β]-7-[3-[(Hexylsulfonyl)methyl]bicyclo[2.2.1]hept-2-yl]-5-heptenoic acid, methyl ester (Example 54)

To a solution of 634 mg (1.72 mmol) of [1β,2α(Z),3α,4β]-7-[3-([hexylthio)methyl]bicyclo[2.2.1]hept-2-yl]-5-heptenoic acid, methyl ester (prepared as described in Example 3) in 6.78 ml of methanol at 0° C. is added dropwise over 4 minutes 8.37 ml of 0.5M aqueous sodium periodate solution. Tetrahydrofuran (2 ml) is then added and the resulting reaction mixture is stirred at room temperature for 15 hours. A precipitate is removed by filtration and washed with ether (3×50 ml). The filtrate is washed with 60 ml of saturated aqueous NaHCO$_3$ solution and dried over anhydrous magnesium sulfate. Concentration in vacuo affords an oily crude product. This is chromatographed on silica gel 60 using 0.5–1.0% CH$_3$OH in CH$_2$Cl$_2$ as eluant. This gives FMI (fast moving isomer) sulfoxide (Example 52) (211 mg, 32%), SMI (slow moving isomer) sulfoxide (Example 53) (142 mg, 21%) and sulfone (Example 54) (165 mg, 24%). These products are oils which solidify on storage in the freezer.

EXAMPLE 55

[1β,2α(Z),3α,4β]-7-[3-[(Hexylsulfonyl)methyl]-bicyclo[2.2.1]hept-2-yl]-5-heptenoic acid To a stirred solution of 165 mg (0.41 mmol) of [1β,2α(Z),3α,4β]-7-[3-[(hexylsulfonyl)methyl]bicyclo[2.2.1]hept-2-yl]-5-heptenoic acid, methyl ester (Example 54) in 20.3 ml of THF and 3.09 ml of H$_2$O under argon is added 3.90 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 30 ml of saturated NaCl solution. The resulting solution is saturated with solid NaCl and extracted with EtOAc (4×50 ml). The combined EtOAc extracts are dried (MgSO$_4$), filtered and concentrated in vacuo to give 165 mg of crude acid. Purification is effected by flash chromatography on 20 g of silica gel 60 using 3% CH$_3$OH in CH$_2$Cl$_2$ as eluant. This affords title acid (145 mg, 91%) which solidifies on storage in the freezer.

EXAMPLE 56

[1β,2α(Z),3α,4β]-7-[3-[(Hexylsulfinyl)methyl]bicyclo[2.2.1]hept-2-yl]-5-heptenoic acid (fast moving isomer)

To a stirred solution of 211 mg (0.55 mmol) of [1β,2α(Z),3α,4β]-7-[3-[(hexylsulfinyl)methyl]bicyclo[2.2.1]hept-2-yl]-5-heptenoic acid, methyl ester (fast moving isomer) prepared in Example 52 in 27.0 ml of THF and 4.11 ml of H$_2$O under argon is added 5.19 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 50 ml of saturated NaCl solution. The resulting solution is saturated with solid NaCl and extracted with EtOAc (4×100 ml). The combined EtOAc extracts are dried (MgSO$_4$), filtered and concentrated in vacuo to give 216 mg of crude acid. Purification is effected by flash chromatography on 20.2 g of silica gel 60 using 3% CH$_3$OH in CH$_2$Cl$_2$ as eluant to give the title acid (172 mg, 85%) as a white solid.

EXAMPLE 57

[1β,2α(Z),3α,4β]-7-[3-[(Hexylsulfinyl)methyl]bicyclo[2.2.1]hept-2-yl]-5-heptenoic acid (slow moving isomer)

To a stirred solution of 142 mg (0.37 mmol) of [1β,2α(Z),3α,4β]-7-[3-[(hexylsulfinyl)methyl]bicyclo[2.2.1]hept-2-yl]-5-heptenoic acid, methyl ester (slow moving isomer) prepared as described in Example 53 in 18.2 ml of THF and 2.77 ml of H$_2$O under argon is added 3.50 ml of 1N aqueous lithium hydroxide solution. This mixture is purged with argon vigorously for 15 minutes and stirred at room temperature for 4 hours and 40 minutes. The reaction mixture is acidified to pH 4 by addition of 1N aqueous HCl solution and poured into 30 ml of saturated NaCl solution. The resulting solution is saturated with solid NaCl and extracted with EtOAc (3×70 ml). The combined EtOAc extracts are dried (MgSO$_4$), filtered and concentrated in vacuo to give 152 mg of crude acid. Purification is effected by flash chromatography on 20.8 g of silica gel 60 using 4% CH$_3$OH in CH$_2$Cl$_2$ as eluant to give title acid.

EXAMPLE 58

[1β,2α(Z),3α,4β]-7-[3-[(Methylsuulfinyl)methyl]bicyclo[2.2.1]hept-2-yl]-5-heptenoic acid (fast moving isomer)

Following the procedure of Examples 3, 52 and 56 except substituting methyl mercaptan for 1-hexanethiol, the title compound is obtained.

EXAMPLE 59

[1β,2α(Z),3α,4β]-7-[3-[(Octylsulfinyl)metyl]bicyclo[2.2.1]hept-2-yl]-5-heptenoic acid (slow moving isomer)

Following the procedure of Examples 3, 53 and 57 except substituting 1-octanethiol for 1-hexanethiol, the title compound is obtained.

EXAMPLE 60

[1β,2α(Z),3α,4β]-7-[3-[(Ethylsulfinyl)methyl]bicyclo[2.2.1]hept-2-yl]-5-heptenoic acid Following the procedure of Examples 3, 52 and 56 except substituting ethylmercaptan for 1-hexanethiol, the title compound is obtained.

EXAMPLE 61

(1β,2α,3α,4β)-7-[3-[(Heptylsulfinyl)methyl]bicyclo[2.2.1]hept-2-yl]heptanoic acid Following the procedure of Examples 3, 2, 52 and 56 except substituting 1-heptanethiol for 1-hexanethiol, the title compound is obtained.

EXAMPLE 62

[1β,2α(Z),3α,4β]-7-[3-[(Benzylsulfinyl)methyl]bicyclo[2.2.1]hept-2-yl]-5-heptenoic acid Following the procedure of Examples 3, 52 and 56 except substituting benzylmercaptan for 1-hexanethiol, the title compound is obtained.

EXAMPLE 63

[1β,2α(Z),3α,4β]-7-[3-[(Cyclohexylmethylsulfinyl)methyl]bicyclo[2.2.1]hept-2-yl]-5-heptenoic acid Following the procedure of Examples 3, 52 and 56 except substituting cyclohexylmethyl mercaptan for 1-hexanethiol, the title compound is obtained.

EXAMPLE 64

[1β,2α(Z),3α,4β]-7-[3-[(Cyclopentylethylsulfinyl)methyl]bicyclo[2.2.1]hept-2-yl]-5-heptenoic acid Following the procedure of Examples 3, 52 and 56 except substituting cyclopentylethyl mercaptan for 1-hexanethiol, the title compound is obtained.

EXAMPLE 65

[1β,2α(Z),3α,4β]-7-[3-[(Octylsulfonyl)methyl]bicyclo[2.2.1]hept-2-yl]-5-heptenoic acid Following the procedure of Examples 3, 54 and 55 except substituting octylmercaptan for 1-hexanethiol, the title compound is obtained.

EXAMPLE 66

[1β,2α(Z),3α,4β]-7-[3-[(Propylsulfonyl)methyl]bicyclo[2.2.1]hept-2-yl]-5-heptenoic acid Following the procedure of Examples 3, 54 and 55 except substituting propylmercaptan for 1-hexanethiol, the title compound is obtained.

EXAMPLE 67

[1β,2α(Z),3α,4β]-7-[3-[(Phenylsulfonyl)methyl]bicyclo[2.2.1]hept-2-yl]-5-heptenoic acid Following the procedure of Examples 3, 54 and 55 except substituting phenylmercaptan for 1-hexanethiol, the title compound is obtained.

EXAMPLE 68

[1β,2α(Z),3α,4β]-7-[3-[(Benzylsulfonyl)methyl]bicyclo[2.2.1]hept-2-yl]-5-heptenoic acid Following the procedure of Examples 3, 54 and 55 except substituting benzylmercaptan for 1-hexanethiol, the title compound is obtained.

EXAMPLE 69

[1β,2α(Z),3α,4β]-7-[3-[(Cyclohexylsulfonyl)methyl]bicyclo[2.2.1]hept-2-yl]-5-heptenoic acid Following the procedure of Examples 3, 54 and 55 except substituting cyclohexylmercaptan for 1-hexanethiol, the title compound is obtained.

EXAMPLE 70

(1β,2α,3α,4β)-7-[3-[(Cyclopropylmethylsulfinyl)methyl]bicyclo[2.2.1]hept-2-yl]heptanoic acid Following the procedure of Examples 3, 2, 52 and 56 except substituting cyclopropylmercaptan for 1-hexanethiol, the title compound is obtained.

EXAMPLE 71

[1β,2α(Z),3α,4β]-7-[3-[2-(Pentylsulfinyl)ethyl]bicyclo[2.2.1]hept-2-yl]-5-heptenoic acid Following the procedure of Examples 41, 3, 52 and 56 except substituting 1-pentanethiol for 1-hexanethiol, the title compound is obtained.

EXAMPLE 72

[1β,2α(Z),3α,4β]-7-[3-[2-(Phenylsulfinyl)ethyl]bicyclo[2.2.1]hept-2-yl]-5-heptenoic acid Following the procedure of Examples 41, 3, 54 and 55 except substituting phenylmercaptan for 1-hexanethiol, the title compound is obtained.

EXAMPLE 73

[1β,2α(Z),3α,4β]-7-[3-[2-(Cyclohexylsulfonyl)ethyl]bicyclo[2.2.1]hept-2-yl]-5-heptenoic acid Following the procedure of Examples 41, 3, 54 and 55 except substituting cyclohexylmercaptan for 1-hexanethiol, the title compound is obtained.

EXAMPLE 74

[1β,2α(Z),3α,4β]-7-[3-[2-(Benzylsulfinyl)ethyl]bicyclo[2.2.1]hept-2-yl]-5-heptenoic acid Following the procedure of Examples 41, 3, 52 and 56 except substituting benzylmercaptan for 1-hexanethiol, the title compound is obtained.

EXAMPLE 75

[1β,2α(Z),3α(E),4β]-7-[3-[[(4-Phenyl-2-butenyl)thio]-methyl]bicyclo[2.2.1]hept-2-yl]-5-heptenoic acid Following the procedure of Example 3 except substituting 4-phenyl-2-butenylthiol for 1-hexanethiol, the title compound is obtained.

EXAMPLE 76

[1β,2α(Z),3α(E),4β]-7-[3-[[(3-Cyclohexyl-2-propenyl)oxy]methyl]bicyclo[2.2.1]hept-2-yl]-5-heptenoic acid Following the procedure of Example 1 except substituting (E)-3-cyclohexyl-2-propenylmesylate for 1-hexane mesylate, the title compound is obtained.

EXAMPLE 77

(1β,2α,3α,4β)-7-[3-[[(4-Cyclohexyl-2-butenyl)thio]methyl]bicyclo[2.2.1]hept-2-yl]heptanoic acid Following the procedure of Examples 3 and 2 except substituting 4-cyclohexyl-2-butenylthiol for 1-hexanethiol, the title compound is obtained.

EXAMPLE 78

[1β,2α(Z),3α,4β]-7-[3-[[(2,3-Dimethyl-2-heptenyl)oxy]methyl]bicyclo[2.2.1]hept-2-yl]-5-heptenoic acid Following the procedure of Example 31 except substituting 2,3-dimethyl-2-heptenylmesylate for 1-hexane mesylate, the title compound is obtained.

EXAMPLE 79

[1β,2α(Z),3α,4β]-7-[3-[[(3-Ethyl-3-octenyl)thio]methyl]bicyclo[2.2.1]hept-2-yl]-5-heptenoic acid Following the procedure of Example 3 except substituting 3-ethyl-3-octenylthiol for 1-hexanethiol, the title compound is obtained.

EXAMPLE 80

(1β,2α,3α,4β)-7-[3-[(5-Phenyl-4-pentenyl)oxy]methyl]-bicyclo[2.2.1]hept-2-yl]heptanoic acid Following the procedure of Examples 1 and 2 except substituting 5-phenyl-4-pentenylmesylate for 1-hexanemesylate, the title compound is obtained.

EXAMPLE 81

[1β,2α(Z),3α,4β]-7-[3-[[(8-Phenyl-5-octynyl)thio]methyl]bicyclo[2.2.1]hept-2-yl]-5-heptenoic acid Following the procedure of Example 3 except substituting 8-phenyl-5-octynylthiol for 1-hexanethiol, the title compound is obtained.

EXAMPLE 82

[1β,2α(Z),3α,4β]-7-[3-[[(9-Cyclohexyl-3-nonynyl)oxy]methyl]bicyclo[2.2.1]hept-2-yl]-5-heptenoic acid Following the procedure of Example 1 except substituting 9-cyclohexyl-3-nonynylmesylate for 1-hexanemesylate, the title compound is obtained.

EXAMPLE 83

(1β,2α,3α,4β)-7-[3-[[(6-Heptynyl)thio]methyl]bicyclo[2.2.1]hept-2-yl]heptanoic acid Following the procedure of Examples 3 and 2 except substituting 6-heptynylthiol for 1-hexanethiol, the title compound is obtained.

EXAMPLE 84

[1β,2α(Z),3α,4β]-7-(3-[[2-(3-Phenyl-2-propenyl)thio]ethyl]bicyclo[2.2.1]hept-2-yl]-5-heptenoic acid Following the procedure of Examples 19 and 3 except substituting the Example 19 part B alcohol for the alcohol used in Example 3 Part B and substituting 3-phenyl-2-propenylthiol for 1-hexanethiol, the title compound is obtained.

EXAMPLE 85

(1β,2α,3α,4β)-7-[3-[[2-(3-Phenyl-2-propenyl)thio]ethyl]bicyclo[2.2.1]hept-2-yl]heptanoic acid Following the procedure of Example 2 except substituting the Example 84 compound for the Example 1 compound, the title compound is obtained.

EXAMPLE 86

[1β,2α(Z),3α,4β]-7-[3-[[2-(6-Phenyl-3-hexynyl)oxy]ethyl]bicyclo[2.2.1]hept-2-yl]-5-heptenoic acid Following the procedure of Examples 19 and 1 except substituting 6-phenyl-3-hexynylmesylate for 1-hexanemesylate, the title compound is obtained.

EXAMPLE 87

(1β,2α,3α,4β)-7-[3-[[2-(2-Ethyl-3-methyl-2-heptenyl)thio]ethyl]bicyclo[2.2.1]hept-2-yl]heptanoic acid Following the procedure of Examples 3, 2 and 19 except substituting 2-ethyl-3-methyl-2-heptenylthiol for 1-hexanethiol, the title compound is obtained.

EXAMPLE 88

[1β,2α(Z),3α,4β]-7-[3-[[2-(3-Cycloheptyl-2-propenyl)thio]ethyl]bicyclo[2.2.1]hept-2-yl]-5-heptenoic acid Following the procedure of Examples 3, 2 and 19 except substituting 3-cycloheptyl-2-propenylthiol for 1-hexanethiol, the title compound is obtained.

EXAMPLE 89

[1β,2α(Z),3α,4β]-7-[3-[[4-(3-Phenyl-2-propenyl)thio]-butyl]bicyclo[2.2.1]hept-2-yl]-5-heptenoic acid Following the procedure of Examples 48 and 3 except substituting the Example 25 Part C alcohol for the alcohol used in Example 3 and substituting 3-phenyl-2-propenylthiol for 1-hexanethiol, the title compound is obtained.

EXAMPLE 90

[1β,2α(Z),3α,4β]-7-[3-[[4-(6-Phenyl-3-hexynyl)oxy]-butyl]bicyclo[2.2.1]hept-2-yl]-5-heptenoic acid Following the procedure of Examples 25 and 1 except substituting 6-phenyl-3-hexynylmesylate for 1-hexanemesylate, the title compound is obtained.

EXAMPLE 91

[1β,2α(Z),3α,4β]-7-[3-[[4-(7-Phenyl-3-heptenyl)thio]-butyl]bicyclo[2.2.1]hept-2-yl]-5-heptenoic acid Following the procedure of Examples 89 and 3 except substituting 7-phenyl-3-heptenylthiol for 3-phenyl-2-propenylthiol, the title compound is obtained.

EXAMPLE 92

(1β,2α,3α,4β)-7-[[4-(6-Hexenyl)thio]butyl]bicyclo[2.2.1]hept-2-yl]heptanoic acid Following the procedure of Examples 3, 2 and 89 except substituting 6-hexenylthiol for 3-phenyl-2-propenylthiol, the title compound is obtained.

EXAMPLE 93

[1β,2α(Z),3α,4β]-7-[3-[[4-(7-Heptynyl)thio]butyl]bicyclo[2.2.1]hept-2-yl]-5-heptenoic acid Following the procedure of Examples 3 and 89 except substituting 7-heptynylthiol for 3-phenyl-2-propenylthiol, the title compound is obtained.

EXAMPLE 94

[1α,2β(Z),3α,4α]-7-[3-(Propyloxy)bicyclo[2.2.1]hept-2-yl]-5-heptenoic acid

Following the procedure of Example 4 except substituting propyl mesylate for n-heptyl mesylate, the title compound is obtained.

EXAMPLE 95

[1α,2β(Z),3α,4α]-7-[3-(Phenyloxy)bicyclo[2.2.1]hept-2-yl]-5-heptenoic acid

Following the procedure of Example 11 except substituting Example 6 part F alcohol for the alcohol used in Example 11, the title compound is obtained.

EXAMPLE 96

[1α,2β(Z),3α,4α]-7-[3-(Benzyloxy)bicyclo[2.2.1]hept-2-yl]-5-heptenoic acid

Following the procedure of Example 4 except substituting benzyl mesylate for n-heptyl mesylate, the title compound is obtained.

EXAMPLE 97

[1α,2β(Z),3α,4α]-7-[3-(Cyclohexyloxy)bicyclo[2.2.1-]hept-2-yl]-5-heptenoic acid

Following the procedure of Example 4 except substituting cyclohexyl mesylate for n-heptyl mesylate, the title compound is obtained.

EXAMPLE 98

[1α,2β(Z),3α,4α]-7-[3-(Cyclopentylmethyloxy)bicyclo[2.2.1]hept-2-yl]-5-heptenoic acid Following the procedure of Example 4 except substituting cyclopentylmethyl mesylate for n-heptyl mesylate, the title compound is obtained.

EXAMPLE 99

[1α,2β(Z),3α,4α]-7-[3-(2,3-Dimethyl-2-heptenyloxy)-bicyclo[2.2.1]hept-2-yl]-5-heptenoic acid Following the procedure of Example 4 except substituting 2,3-dimethyl-2-heptenyl mesylate for n-heptyl mesylate, the title compound is obtained.

EXAMPLE 100

[1α,2β(Z),3α,4α]-7-[3-(6-Heptynyloxy)bicyclo[2.2.1-]hept-2-yl]-5-heptenoic acid

Following the procedure of Example 4 except substituting 6-heptynyl mesylate for n-heptyl mesylate, the title compound is obtained.

EXAMPLE 101

[1β,2α(Z),3α,4β]-7-[3-(Octyloxy)bicyclo[2.2.1]hept-2-yl]-5-heptenoic acid

Following the procedure of Example 5 except substituting octyl mesylate for n-heptyl mesylate, the title compound is obtained.

EXAMPLE 102

[1β,2α(Z),3α,4β]-7-[3-(Phenyloxy)bicyclo[2.2.1]hept-2-yl]-5-heptenoic acid

Following the procedure of Example 11 except substituting Example 7 part B alcohol for the alcohol in Example 11, the title compound is obtained.

EXAMPLE 103

[1β,2α(Z),3α,4β]-7-[3-(Phenylpropoxy)bicyclo[2.2.1-]hept-2-yl]-5-heptenoic acid

Following the procedure of Example 5 except substituting phenyl propyl mesylate for n-heptyl mesylate, the title compound is obtained.

EXAMPLE 104

[1β,2α(Z),3α,4β]-7-[3-(Cyclohexyloxy)bicyclo[2.2.1-]hept-2-yl]-5-heptenoic acid

Following the procedure of Example 5 except substituting cyclohexyl mesylate for n-heptyl mesylate, the title compound is obtained.

EXAMPLE 105

[1β,2α(Z),3α,4β]-7-[3-(Cyclopentylethyloxy)bicyclo[2.2.1]hept-2-yl]-5-heptenoic acid Following the procedure of Example 5 except substituting cyclopentylethyl mesylate for n-heptyl mesylate, the title compound is obtained.

EXAMPLE 106

[1β,2α(Z),3α,4β]-7-[3-(2-Propenyloxy)bicyclo[2.2.1-]hept-2-yl]-5-heptenoic acid

Following the procedure of Example 5 except substituting 2-propenyl mesylate for n-heptyl mesylate, and title compound is obtained.

EXAMPLE 107

[1β,2α(Z),3α,4β]-7-[3-(6-Heptynyloxy)bicyclo[2.2.1-]hept-2-yl]-5-heptenoic acid

Following the procedure of Example 5 except substituting 6-heptynyl mesylate for n-heptyl mesylate, the title compound is obtained.

EXAMPLE 108

(1α,2β,3β,4α)-7-[3-(Pentyloxy)bicyclo[2.2.1]hept-2-yl]-5-heptenoic acid

Following the procedure of Examples 5 and 2 except substituting pentyl mesylate for n-heptyl mesylate, the title compound is obtained.

EXAMPLE 109

(1α,2β,3β,4α)-7-[3-(Phenyloxy)bicyclo[2.2.1]hept-2-yl]heptanoic acid

Following the procedure of Examples 11 and 2 except substituting Example 7 part B alcohol for the acid in Example 2 and substituting this product for the alcohol used in Example 11, the title compound is obtained.

EXAMPLE 110

(1α,2β,3β,4α)-7-[3-(Benzyloxy)bicyclo[2.2.1]hept-2-yl]heptanoic acid

Following the procedure of Examples 5 and 2 except substituting benzyl mesylate for n-heptyl mesylate, the title compound is obtained.

EXAMPLE 111

(1α,2β,3β,4α)-7-[3-(cyclopentyloxy)bicyclo[2.2.1]hept-2-yl]heptanoic acid

Following the procedure of Examples 5 and 2 except substituting cyclopentyl mesylate for n-heptyl mesylate, the title compound is obtained.

EXAMPLE 112

(1α,2β,3β,4α)-7-[3-(Cyclohexylmethyloxy)bicyclo[2.2.1]hept-2-yl]heptanoic acid

Following the procedure of Examples 5 and 2 except substituting cyclohexylmethyl mesylate for n-heptyl mesylate, the title compound is obtained.

EXAMPLE 113

(1α,2β,3β,4α)-7-[3-(3-Ethyl-3-octenyloxy)bicyclo[2.2.1]hept-2-yl]heptanoic acid

Following the procedure of Examples 5 and 2 except substituting 3-ethyl-3-octenyl mesylate for n-heptyl mesylate, the title compound is obtained.

EXAMPLE 114

(1α,2β,3β,4α)-7-[3-(5-Octynyloxy)bicyclo[2.2.1]hept-2-yl]heptanoic acid

Following the procedure of Examples 5 and 2 except substituting 5-octynyl mesylate for n-heptyl mesylate, the title compound is obtained.

EXAMPLE 115

[1α,2β(Z),3α,4α]-7-(Butylthio)bicyclo[2.2.1]hept-2-yl]-5-heptenoic acid

Following the procedure of Example 6 except substituting butylbromide for n-heptyl bromide, the title compound is obtained.

EXAMPLE 116

[1α,2β(Z),3α,4α]-7-[3-(Benzylthio)bicyclo[2.2.1]hept-2-yl]-5-heptenoic acid

Following the procedure of Example 6 except substituting benzylbromide for n-heptylbromide, the title compound is obtained.

EXAMPLE 117

[1α,2β(Z),3α,4α]-7-[3-(Cyclopentylthio)bicyclo[2.2.1]hept-2-yl]-5-heptenoic acid Following the procedure of Example 6 except substituting cyclopentylbromide for n-heptylbromide, the title compound is obtained.

EXAMPLE 118

[1α,2β(Z),3α,4α]-7-[3-(Cyclohexylmethylthio)bicyclo[2.2.1]hept-2-yl]-5-heptenoic acid Following the procedure of Example 6 except substituting cyclohexylmethylbromide for n-heptylbromide, the title compound is obtained.

EXAMPLE 119

[1α,2β(Z),3α,4α]-7-[3-(4-Pentenylthio)bicyclo[2.2.1]hept-2-yl]-5-heptenoic acid

Following the procedure of Example 6 except substituting 4-pentenylbromide for n-heptylbromide, the title compound is obtained.

EXAMPLE 120

[1α,2β(Z),3α,4α]-7-[3-(3-Heptynylthio)bicyclo[.2.1]hept-2-yl]-5-heptenoic acid

Following the procedure of Example 6 except substituting 3-heptynylbromide for n-heptylbromide, the title compound is obtained.

EXAMPLE 121

[1β,2α(Z),3α,4β]-7-[3-(Nonylthio)bicyclo[2.2.1]hept-2-yl]-5-heptenoic acid

Following the procedure of Example 7 except substituting nonylthiol for n-heptanethiol, the title compound is obtained.

EXAMPLE 122

[1β,2α(Z),3α,4β]-7-[3-(Phenylthio)bicyclo[2.2.1]hept-2-yl]-5-heptenoic acid

Following the procedure of Example 7 except substituting phenylthiol for n-heptanethiol, the title compound is obtained.

EXAMPLE 123

[1β,2α(Z),3α,4β]-7-[3-(Phenethylthio)bicyclo[2.2.1]hept-2-yl]-5-heptenoic acid

Following the procedure of Example 7 except substituting phenethylthiol for n-heptanethiol, the title compound is obtained.

EXAMPLE 124

[1β,2α(Z),3α,4β]-7-[3-(Cyclohexylthio)bicyclo[2.2.1]hept-2-yl]-5-heptenoic acid

Following the procedure of Example 7 except substituting cyclohexylthiol for n-heptanethiol, the title compound is obtained.

EXAMPLE 125

[1β,2α(Z),3α,4β]-7-[3-(Cyclopentylmethylthio)bicyclo[2.2.1]hept-2-yl]-5-heptenoic acid Following the procedure of Example 7 except substituting cyclopentylmethylthiol for n-heptanethiol, the title compound is obtained.

EXAMPLE 126

[1β,2α(Z),3α,4β]-7-[3-(2-Butenylthio)bicyclo[2.2.1]hept-2-yl]-5-heptenoic acid

Following the procedure of Example 7 except substituting 2-butenylthiol for n-heptanethiol, the title compound is obtained.

EXAMPLE 127

[1β,2α(Z),3α,4β]-7-[3-(5-Hexynylthio)bicyclo[2.2.1]hept-2-yl]-5-heptenoic acid

Following the procedure of Example 7 except substituting 5-hexynylthiol for n-heptanethiol, the title compound is obtained.

EXAMPLE 128

(1α,2β,3β,4α)-7-[3-(Propylthio)bicyclo[2.2.1]hept-2-yl]heptanoic acid

Following the procedure of Examples 7 and 2 except substituting propylthiol for n-heptanethiol, the title compound is obtained.

EXAMPLE 129

(1α,2β,3β,4α)-7-[3-(Phenylthio)bicyclo[2.2.1]hept-2-yl]heptanoic acid

Following the procedure of Examples 7 and 2 except substituting phenylthiol for n-heptanethiol, the title compound is obtained.

EXAMPLE 130

[1α,2β(Z),3β,4α]-7-[3-(3-Methylbenzylthio)bicyclo[2.2.1]hept-2-yl]-5-heptenoic acid Following the procedure of Examples 7 except substituting 3-methylbenzylthiol for n-heptanethiol, the title compound is obtained.

EXAMPLE 131

(1α,2β,3β,4α)-7-[3-(Cyclohexylthio)bicyclo[2.2.1]hept-2-yl]heptanoic acid

Following the procedure of Examples 7 and 2 except substituting cyclohexylthiol for n-heptanethiol, the title compound is obtained.

EXAMPLE 132

(1α,2β, 3β,4α)-b 7-[3-(Cycloheptylmethylthio)bicyclo[2.2.1]hept-2-yl]heptanoic acid Following the procedure of Examples 7 and 2 except substituting cycloheptylmethylthiol for n-heptanethiol, the title compound is obtained.

EXAMPLE 133

(1α,2β,3β,4α)-7-[3-(2-Pentenylthio)bicyclo[2.2.1]hept-2-yl]heptanoic acid

Following the procedure of Examples 7 and 2 except substituting 2-pentenylthiol for n-heptanethiol, the title compound is obtained.

EXAMPLE 134

(1α,2β,3β,4α)-7-[3-(4-Pentynylthio)bicyclo[2.2.1]hept-2-yl]heptanoic acid

Following the procedure of Examples 7 and 2 except substituting 4-pentynylthiol for n-heptanethiol, the title compound is obtained.

It will also be appreciated that the carboxybutyl triphenylphosphonium bromide of the structure

employed in forming the upper side chain in the aforementioned examples may be replaced by

wherein $(CH_2)_n$ is defined hereinbefore, to form compounds of the invention wherein the upper side chain is of the structure

What is claimed is:

1. A compound of the structure

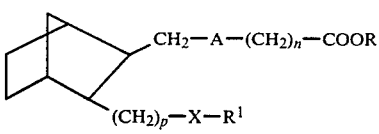

including all stereoisomers thereof, wherein A is —CH=CH— or —CH$_2$—CH$_2$—; n is 0 to 8; p is 0 or 1; X is O or

wherein q is 0, 1 or 2; R is H, lower alkyl, alkali metal or tris(hydroxymethyl)aminomethane; and $R^1$ is lower alkyl, aryl, arylalkyl, cycloalkyl, cycloalkylalkyl, lower alkenyl containing 2 to 12 carbons or lower alkynyl containing 2 to 12 carbons, wherein lower alkyl or alkyl alone or as part of another group contains 1 to 12 carbons and is unsubstituted or is substituted with halo, CF$_3$ alkoxy, aryl, alkyl-aryl, haloaryl, cycloalkyl or alkylcycloalkyl;

aryl alone or as part of another group contains 6 to 10 carbons in the ring portion and is unsubstituted or is substituted with 1 or 2 lower alkyl groups, 1 or 2 halogens and/or 1 or 2 lower alkoxy groups; and cycloalkyl alone or as part of another group contains 3 to 12 carbons and is unsubstituted or is substituted with 1 or 2 halogens, 1 or 2 lower alkyl groups and/or 1 or 2 lower alkoxy groups.

2. The compound as defined in claim 1 wherein X is O.

3. The compound as defined in claim 1 wherein X is S.

4. The compound as defined in claim 1 wherein p is 1.

5. The compound as defined in claim 1 wherein n is 3 to 5.

6. The compound as defined in claim 1 wherein A is CH$_2$—CH$_2$ or CH=CH, p is 0 or 1, n is 3 to 5, R is H and $R^1$ is lower alkyl.

7. The compound as defined in claim 1 wherein $R^1$ is butyl, pentyl, hexyl or heptyl including all isomers thereof.

8. The compound as defined in claim 1 having the name [1β,2α(Z),3α,4β]-7-[3-[(hexyloxy)methyl]bicyclo[2.2.1]hept-2-yl]-5-heptenoic acid or the methyl ester or hexyl ester thereof including all stereoisomers thereof.

9. The compound as defined in claim 1 having the name (1α,2β,3β,4α)-7-[3-[(hexyloxy)methyl]bicyclo[2.2.1]hept-2-yl]heptanoic acid including all stereoisomers thereof.

10. The compound as defined in claim 1 [1β,2α(Z)-,3α,4β]-7-[3-[(hexylthio)methyl]bicyclo[2.2.1]hept-2-yl]-5-heptenoic acid or the methyl ester thereof including all stereoisomers thereof.

11. The compound as defined in claim 1 having the name [1α,2β(Z),3α,4α]-7-[3-(heptyloxy)bicyclo[2.2.1-]hept-2-yl]-5-heptenoic acid or the methyl esters thereof including all stereoisomers thereof.

12. The compound as defined in claim 1 having the name [1α,2β(Z),3β,4α]-7-[3-(heptyloxy)bicyclo[2.2.1-

]hept-2-yl]-5-heptenoic acid or the methyl ester thereof including all stereoisomers thereof.

13. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

14. The method as defined in claim 10 wherein said compound is administered in an amount within the range of from about 1 to about 100 mg/kg.

15. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

16. A method of inhibiting platelet aggregation which comprises administering to a mammalian host an effective amount of a compound as defined in claim 1 or a pharmaceutically acceptable salt thereof.

17. A method of inhibiting bronchoconstriction associated with asthma, which comprises administering to a mammalian host an effective amount of a compound as defined in claim 1 or a pharmaceutically acceptable salt thereof.

18. A method for treating peripheral vascular disease, which comprises topically or systemically administering to a mammalian host an effective amount of a compound as defined in claim 1 or a pharmaceutically acceptable salt thereof.

* * * * *